US011852634B2

(12) United States Patent
Ovadia et al.

(10) Patent No.: US 11,852,634 B2
(45) Date of Patent: Dec. 26, 2023

(54) USE OF AKT PHOSPHORYLATION AS A BIOMARKER FOR PROGNOSING NEURODEGENERATIVE DISEASES AND TREATING SAME

(71) Applicants: Yeda Research and Development Co. Ltd., Rehovot (IL); Universitätsklinikum Hamburg-Eppendorf, Hamburg (DE)

(72) Inventors: Eran Ovadia, Mevasseret Zion (IL); Irun R. Cohen, Rehovot (IL); Johannes Herkel, Hamburg (DE); Raanan Margalit, Rehovot (IL); Meirav Pevsner-Fischer, Nes Ziona (IL)

(73) Assignees: Yeda Research and Development Co. Ltd., Rehovot (IL); Universitätsklinikum Hamburg-Eppendorf, Hamburg (DE)

( * ) Notice: Subject to any disclaimer, the term of this patent is extended or adjusted under 35 U.S.C. 154(b) by 409 days.

(21) Appl. No.: 17/081,013

(22) Filed: Oct. 27, 2020

(65) Prior Publication Data
US 2021/0041455 A1 Feb. 11, 2021

Related U.S. Application Data

(62) Division of application No. 16/352,879, filed on Mar. 14, 2019, now abandoned, which is a division of application No. 14/883,685, filed on Oct. 15, 2015, now Pat. No. 10,288,622, which is a division of application No. 14/119,891, filed as application No. PCT/IL2012/050185 on May 23, 2012, now abandoned.

(60) Provisional application No. 61/488,806, filed on May 23, 2011.

(51) Int. Cl.
| | |
|---|---|
| *G01N 33/68* | (2006.01) |
| *A61K 38/08* | (2019.01) |
| *A61K 38/18* | (2006.01) |
| *A61K 31/343* | (2006.01) |
| *A61K 38/30* | (2006.01) |
| *A61K 45/06* | (2006.01) |
| *C07K 7/06* | (2006.01) |
| *G01N 33/543* | (2006.01) |

(52) U.S. Cl.
CPC ....... *G01N 33/6854* (2013.01); *A61K 31/343* (2013.01); *A61K 38/08* (2013.01); *A61K 38/185* (2013.01); *A61K 38/1808* (2013.01); *A61K 38/1825* (2013.01); *A61K 38/1833* (2013.01); *A61K 38/1841* (2013.01); *A61K 38/1866* (2013.01); *A61K 38/1891* (2013.01); *A61K 38/30* (2013.01); *A61K 45/06* (2013.01); *C07K 7/06* (2013.01); *G01N 33/54306* (2013.01); *G01N 33/6896* (2013.01); *G01N 2800/28* (2013.01); *G01N 2800/52* (2013.01)

(58) Field of Classification Search
CPC ......... G01N 33/6854; G01N 33/54306; G01N 33/6896; G01N 2800/28; G01N 2800/52; A61K 31/343; A61K 38/08; A61K 38/1808; A61K 38/1825; A61K 38/1833; A61K 38/1841; A61K 38/185; A61K 38/1866; A61K 38/1891; A61K 38/30; A61K 45/06; C07K 7/06
See application file for complete search history.

(56) References Cited

U.S. PATENT DOCUMENTS

| | | |
|---|---|---|
| 4,946,778 A | 8/1990 | Ladner et al. |
| 5,091,513 A | 2/1992 | Huston et al. |
| 5,096,815 A | 3/1992 | Ladner et al. |
| 5,223,409 A | 6/1993 | Ladner et al. |
| 5,338,665 A | 8/1994 | Schatz et al. |
| 5,432,018 A | 7/1995 | Dower et al. |
| 5,498,530 A | 3/1996 | Schatz et al. |
| 5,733,731 A | 3/1998 | Schatz et al. |
| 5,910,573 A | 6/1999 | Plueckthun |
| 5,922,545 A | 7/1999 | Mattheakis et al. |
| 6,294,353 B1 | 9/2001 | Pack et al. |
| 6,420,136 B1 | 7/2002 | Riabowol et al. |
| 6,593,353 B1 | 7/2003 | Gudkov et al. |
| 6,630,584 B1 | 10/2003 | Solomon et al. |
| 6,723,567 B1 | 4/2004 | Harr et al. |
| 6,726,895 B2 | 4/2004 | Strauss et al. |
| 7,030,090 B2 | 4/2006 | Ryu et al. |

(Continued)

FOREIGN PATENT DOCUMENTS

| | | |
|---|---|---|
| CN | 1692126 | 11/2005 |
| EP | 1408114 | 4/2004 |

(Continued)

OTHER PUBLICATIONS

Advisory Action Before the Filing of an Appeal Brief dated Dec. 1, 2017 From the US Patent and Trademark Office Re. U.S. Appl. No. 14/883,685. (3 pages).

(Continued)

*Primary Examiner* — Olga N Chernyshev

(57) ABSTRACT

The present invention relates to uses of a peptide comprising an amino acid sequence selected from the group consisting of SEQ ID NO: 1, SEQ ID NO: 2, analogues and derivatives thereof, for the treatment of neurodegenerative diseases, such as amyotrophic lateral sclerosis (ALS). The present invention further provides a method for assessing responsiveness to treatment with the peptide of the invention. In addition, the present invention relates to prognosis of ALS progression, using Akt and phosphorylated Akt as biomarkers.

3 Claims, 4 Drawing Sheets
Specification includes a Sequence Listing.

(56) References Cited

U.S. PATENT DOCUMENTS

| | | | |
|---|---|---|---|
| 7,517,857 | B2 | 4/2009 | Ryu et al. |
| 7,622,455 | B2 | 11/2009 | Bennett et al. |
| 7,659,243 | B2 | 2/2010 | Greenway et al. |
| 2005/0281816 | A1 | 12/2005 | Lamping et al. |
| 2006/0014719 | A1 | 1/2006 | Chang |
| 2008/0045456 | A1 | 2/2008 | Greenway et al. |
| 2008/0267983 | A1 | 10/2008 | Herkel et al. |
| 2009/0169649 | A1 | 7/2009 | Hovens et al. |
| 2009/0324549 | A1 | 12/2009 | Battaglia et al. |
| 2010/0009364 | A1 | 1/2010 | Fantl et al. |
| 2010/0099700 | A1 | 4/2010 | Hung |
| 2010/0292281 | A1 | 11/2010 | Lovell et al. |
| 2010/0298306 | A1 | 11/2010 | Herbert et al. |
| 2012/0171233 | A1 | 7/2012 | Herkel et al. |
| 2014/0088017 | A1 | 3/2014 | Ovadia et al. |
| 2014/0329758 | A1 | 11/2014 | Kerkel et al. |
| 2015/0297693 | A1 | 10/2015 | Herkel et al. |
| 2016/0033529 | A1 | 2/2016 | Ovadia et al. |
| 2019/0204340 | A1 | 7/2019 | Ovadia et al. |

FOREIGN PATENT DOCUMENTS

| | | |
|---|---|---|
| JP | 2006-505503 | 2/2006 |
| WO | WO 94/12202 | 6/1994 |
| WO | WO 96/37621 | 11/1996 |
| WO | WO 96/40987 | 12/1996 |
| WO | WO 98/15833 | 4/1998 |
| WO | WO 98/52558 | 11/1998 |
| WO | WO 98/56416 | 12/1998 |
| WO | WO 99/23091 | 5/1999 |
| WO | WO 99/32463 | 7/1999 |
| WO | WO 00/23082 | 4/2000 |
| WO | WO 01/01986 | 1/2001 |
| WO | WO 03/099868 | 12/2003 |
| WO | WO 2004/035793 | 4/2004 |
| WO | WO 2006/021954 | 3/2006 |
| WO | WO 2006/054277 | 5/2006 |
| WO | WO 2009/117387 | 9/2009 |
| WO | WO 2011/017030 | 2/2011 |
| WO | WO 2011/028912 | 3/2011 |
| WO | WO 2012/160563 | 11/2012 |

OTHER PUBLICATIONS

Advisory Action Before the Filing of an Appeal Brief dated Sep. 21, 2015 From the US Patent and Trademark Office Re. U.S. Appl. No. 14/119,891.
Applicant-Initiated Interview Summary dated Dec. 3, 2018 From the US Patent and Trademark Office Re. U.S. Appl. No. 14/883,685. (3 pages).
Communication Pursuant to Article 94(3) EPC dated Feb. 6, 2015 From the European Patent Office Re. Application No. 11181049.5.
Communication Pursuant to Article 94(3) EPC dated Feb. 11, 2013 From the European Patent Office Re. Application No. 05774723.0.
Communication Pursuant to Article 94(3) EPC dated Feb. 22, 2016 From the European Patent Office Re. Application No. 12788741.2.
Communication Pursuant to Article 94(3) EPC dated Oct. 28, 2015 From the European Patent Office Re. Application No. 11181049.5.
Communication Pursuant to Article 94(3) EPC dated Jul. 30, 2018 From the European Patent Office Re. Application No. 17183041.7. (4 Pages).
European Search Report and the European Search Opinion dated Mar. 11, 2013 From the European Patent Office Re. Application No. 11181049.5.
European Search Report and the European Search Opinion dated Sep. 29, 2017 From the European Patent Office Re. Application No. 17183041.7. (8 Pages).
Examination Report dated Jul. 17, 2012 From the Government of India, Patent Office, Intellectual Property Building Re. Application No. 1729/DELNP/2007.
Examiner's Report dated Aug. 16, 2011 From the Australian Government, IP Australia Re. Application No. 2005276117.
Hearing Notice dated Jan. 17, 2014 From the Government of India, Patent Office, Intellectual Property Building Re. Application No. 1729/DELNP/2007.
International Preliminary Report on Patentability dated Apr. 3, 2014 From the International Bureau of WIPO Re. Application No. PCT/IL2012/050185.
International Preliminary Report on Patentability dated Feb. 28, 2007 From the International Bureau of WIPO Re. Application No. PCT/IL2005/000908.
International Search Report and the Written Opinion dated Nov. 7, 2006 From the International Searching Authority Re. Application No. PCT/IL2005/000908.
International Search Report and the Written Opinion dated Oct. 9, 2012 From the International Searching Authority Re. Application No. PCT/IL2012/050185.
Office Action dated Jun. 23, 2014 From the Israel Patent Office Re. Application No. 1281471 and Its Translation Into English.
Official Action dated Jul. 3, 2018 From the US Patent and Trademark Office Re. U.S. Appl. No. 14/883,685. (12 pages).
Official Action dated Jul. 5, 2013 From the US Patent and Trademark Office Re. U.S. Appl. No. 13/287,098.
Official Action dated Oct. 7, 2010 From the US Patent and Trademark Office Re. U.S. Appl. No. 11/573,707.
Official Action dated Dec. 9, 2013 From the US Patent and Trademark Office Re. U.S. Appl. No. 13/287,098.
Official Action dated Feb. 10, 2011 From the US Patent and Trademark Office Re. U.S. Appl. No. 11/573,707.
Official Action dated Apr. 12, 2017 from the US Patent and Trademark Office Re. U.S. Appl. No. 14/883,685. (29 pages).
Official Action dated Jul. 15, 2015 From the US Patent and Trademark Office Re. U.S. Appl. No. 14/119,891.
Official Action dated Dec. 18, 2014 From the US Patent and Trademark Office Re. U.S. Appl. No. 14/119,891.
Official Action dated Oct. 19, 2018 From the US Patent and Trademark Office Re. U.S. Appl. No. 14/883,685. (9 pages).
Official Action dated Sep. 22, 2017 from the US Patent and Trademark Office Re. U.S. Appl. No. 14/883,685. (11 Pages).
Official Action dated Jan. 26, 2018 From the US Patent and Trademark Office Re. U.S. Appl. No. 14/883,685. (10 pages).
Official Action dated Jun. 30, 2016 From the US Patent and Trademark Office Re. U.S. Appl. No. 14/754,835.
Official Action dated Dec. 31, 2014 From the US Patent and Trademark Office Re. U.S. Appl. No. 14/341,814.
Official Action dated Apr. 8, 2020 from the US Patent and Trademark Office Re. U.S. Appl. No. 16/352,879. (22 pages).
Requisition by the Examiner dated Mar. 19, 2019 From the Innovation, Science and Economic Development Canada, Canadian Intellectual Property Office Re. Application No. 2,836,503. (5 Pages).
Requisition by the Examiner dated Mar. 23, 2018 From the Innovation, Science and Economic Development Canada, Canadian Intellectual Property Office Re. Application No. 2,836,503. (9 Pages).
Search Report dated Feb. 14, 2014 From the State Intellectual Property Office of the People's Republic of China Re. Application No. 201310079356.4 and Its Translation Into English.
Supplementary European Search Report and the European Search Opinion dated Jul. 2, 2015 From the European Patent Office Re. Application No. 12788741.2.
Supplementary European Search Report and the European Search Opinion dated Jun. 23, 2009 From the European Patent Office Re. Application No. 05774723.0.
Supplementary Partial European Search Report dated Mar. 26, 2015 From the European Patent Office Re. Application No. 12788741.2.
Translation of Decision of Rejection dated Dec. 5, 2012 From the State Intellectual Property Office of the People's Republic of China Re. Application No. 200580028458.7.
Translation of Official Action dated Nov. 16, 2010 From the Japanese Patent Office Re. Application No. 2007-529133.
Baker et al. "Suppression of Human Colorectal Carcinoma Cell Growth by Wild-Type P53", Science, New Series, 249(4971): 912-915, Aug. 24, 1990.

(56) References Cited

OTHER PUBLICATIONS

Bhaskar et al. "The PI3K-Akt-mTOR Pathway Regulates A[Beta] Oligomer Induced Neuronal Cell Cycle Events", Molecular Neurodegeneration, XP021052327, 4(14): 1-18, Mar. 16, 2009. p. 7, Left Col., Middle Para.

Bruijn et al. "Unraveling the Mechanisms Involved in Motor Neuron Degeneration in ALS", Annual Review in Neuroscience, 27: 723-749, 2004.

Brunet et al. "Transcription-Dependent and -Independent Control of Neuronal Survival by the PI3K-Akt Signaling Pathway", Current Opinion in Neurobiology, 11(3): 297-305, Jun. 2001.

Casset et al. "A Peptide Mimetic of An Anti-CD4 Monoclonal Antibody by Rational Design", Biochemical and Biophysical Research Communications, 307: 198-205, 2003.

Castri et al. "Reduced Insulin-Induced Phosphatidylinositol-3-Kinase Activation in Peripheral Blood Mononuclear Leucocytes From Patients with Alzheimer's Disease", European Journal of Neuroscience, 26(9): 2469-2472, Nov. 2007.

Cohen "Discrimination and Dialogue in the Immune System", Seminars in Immunology, 12(3): 215-219, Jun. 2000.

Crameri et al. "Modular Antigen Transporter Molecule Protein Seq ID No. 16", A-Geneseq_8, Accession No. ADM57310, 1 P., Jul. 1, 2004.

Cwirla et al. "Peptide Agonist of the Thrombopoietin Receptor as Potent as the Natural Cytokine", Science, New Series, 276(5319): 1696-1699, Jun. 13, 1997.

Dedman et al. "Selection of Targeted Biological Modifiers From A Bacteriophage Library of Random Peptides", The Journal of Biological Chemistry, 268(31): 23025-23030, Nov. 5, 1993.

Devlin et al. "Random Peptide Libraries: A Source of Specific Protein Binding Molecules", Science, New Series, 249(4967): 404-406, Jul. 27, 1990.

Dewil et al. "Vascular Endothelial Growth Factor Counteracts the Loss of Phospho-Akt Preceding Motor Neurone Degeneration in Amyotrophic Lateral Sclerosis", Neuropathology and Applied Neurobiology, 33(5): 499-509, Oct. 2007.

Dinarello "Interleukin-1", Reviews of Infectious Diseases, 6(1): 51-95, Jan.-Feb. 1984.

Dobrowolny et al. "Muscle Atrophy Induced by SOD1[G93A] Expression Does Not Involve the Activation of Caspase in the Absence of Denervation", Skeletal Muscle, XP021091524, 1(3): 1-8, Jan. 24, 2011.

El-Deiry et al. "Definition of A Consensus Binding Site for p53", Nature Genetics, 1(1): 45-49, Apr. 1992.

Ellis et al. "Mechanisms and Functions of Cell Death", Annual Reviews of Cell Biology, &: 663-698, 1991.

Ershler et al. "Immunologic Aspects of Osteoporosis", Developmental & Comparative Immunology, 21(6): 487-499, Nov.-Dec. 1997.

Foord et al. "A DNA Binding Domain Is Contained in the C-Terminus of Wild Type p53 Protein", Nucleic Acids Research, 19(19): 5191-5198, Oct. 11, 1991.

Gavrieli et al. "Identification of Programmed Cell Death In Situ Via Specific Labeling of Nuclear DNA Fragmentation", The Journal of Cell Biology, 119(3): 493-501, Nov. 1992.

Gruol et al. "Physiological and Pathological Roles of Interleukin-6 in the Central Nervous System", Molecular Neurobiology, 15(3): 307-339, Dec. 1997.

Haunstetter et al. "Apoptosis: Basic Mechanisms and Implications for Cardiovascular Disease", Circulation Research, 82(11): 1111-1129, Jun. 15, 1998.

Herkel et al. "Monoclonal Antibody to A DNA-Binding Domain of P53 Mimics Charge Structure of DNA: Anti-Idiotypes to the Anti-P53 Antibody Are Anti-DNA", European Journal of Immunology, XP002531401, 34(12): 3623-3632, Dec. 2004.

Herkel et al. "Systemic Lupus Erythematosus in Mice, Spontaneous and Induced, Is Associated With Autoimmunity to the C-Terminal Domain of P53 That Recognizes Damaged DNA", European Journal of Immunology, XP002276106, 30(4): 977-984, Apr. 1, 2000.

Hollstein et al. "P53 Mutations in Human Cancers", Science, New Series, 253(5015): 49-53, Jul. 5, 1991.

Kastan et al. "Participation of p53 Protein in the Cellular Response to DNA Damage", Cancer Research, 51(23 Pt.1): 6304-6311, Dec. 1, 1991.

Kastin et al. "Peptides Crossing the Blood-Brain Barrier: Some Unusual Observations", Brain Research, 848(1-2): 96-100, Nov. 27, 1999. Abstract.

Katsnelson "Experimental Autoimmune Encephalomyelitis", Multiple Sclerosis Discovery Forum, p. 1-4, Oct. 23, 2012.

Kay et al. "From Peptide to Drugs Via Phage Display", Drug Discovery Today, DDT, 3(8): 370-378, Aug. 1998.

Ko et al. "P53: Puzzle and Paradigm", Genes & Development, 10(9): 1054-1072, May 1, 1996.

Komarova et al. "Chemoprotection From p53-Dependent Apoptosis: Potential Clinical Applications of the p53 Inhibitors", Biochemical Pharmacology, 62(6): 657-667, May 1, 1996.

Kuerbitz et al. "Wild-Type p53 Is A Cell Cycle Checkpoint Determinant Following Irradiation", Proc. Natl. Acad. Sci. USA, 89(16): 7491-7495, Aug. 15, 1992.

Lee et al. "P53 and Its 14 kDa C-Terminal Domain Recognize Primary DNA Damage in the Form of Insertion/Deletion Mismatches", Cell, 81(7): 1013-1020, Jun. 30, 1995.

Lee et al. "Peptide Recognition by An Anti-Idiotypic Antibody Against Angiotensin II: Peptide Library Search for Peptides Other Than Angiotensin II", Biophysical Journal, XP009118036, 68(2 Pt.2): A406, Th-Pos227, 1995. & 39th Annual Meeting of the Biophysical Society, San Francisco, CA, USA, Feb. 1995.

Leger et al. "Human Skeletal Muscle Atrophy in Amyotrophic Lateral Sclerosis Reveals A Reduction in Akt and An Increase in Atrogin-1", The FASEB Journal, 20(3): 583-585, Jan. 17, 2006.

Liu et al. "Low Avidity Recognition of Self Antigen by T Cells Permits Escape From Central Tolerance", Immunity, 3: 407-415, Oct. 1995.

Lomas et al. "Phase I Clinical Trial of A Human Idiotypic P53 Vaccine in Patients With Advanced Malignancy", Annals of Oncology, XP002531400, 15(2): 324-329, Feb. 2004. p. 325, § 1.

Lowman "Bacteriophage Display and Discovery of Peptide Leads for Drug Development", Annual Review of Biophysics and Biomolecular Structure, 26: 401-424, 1997.

Martin "Neuronal Cell Death in Nervous System Development, Disease, and Injury (Review)", International Journal of Molecular Medicine, 7(5): 455-478, May 2001.

Martin et al. "P53 Is Abnormally Elevated and Active in the CNS of Patients With Amyotrophic Lateral Sclerosis", Neurobiology of Disease, XP055222864, 7(6): 613-622, Dec. 2000.

Mattson et al. "Neurodegenrative Disorders and Ischemic Brain Diseases", Apoptosis, 6(1-2): 69-81, Feb.-Apr. 2001.

Mayo Clinic Staff "Infertility: Causes", Mayo Clinic, 3 P., 1998-2013.

Nathan "Points of Control in Inflammation", Nature, 420(6917): 846-852, Dec. 19-26, 2002.

Nickells "Apoptosis of Retinal Ganglion Cells in Glaucoma: An Update of the Molecular Pathways Involved in Cell Death", Survey of Ophthalmology, 43(Suppl.1): S151-S161, Jun. 1999.

Nicoletti et al. "A Rapid and Simple Method for Measuring Thymocyte Apoptosis by Propidium Iodide Staining and Flow Cytometry", Journal of Immunological Methods, 139(2): 271-279, Jun. 3, 1991.

Nitta et al. "Heat Shock Induces Transient p53-Dependent Cell Cycle Arrest at G1/S", Oncogene, 15(5): 561-568, Jul. 31, 1997.

Pisetsky "The Immunologic Properties of DNA", Journal of Immunology, 156(2): 421-423, Jan. 15, 1996.

Radic et al. "Genetic and Structural Evidence for Antigen Selection of Anti-DNA Antibodies", Annual Review of Immunology. 12: 487-520, 1994.

Raghupathi et al. "Apoptosis After Traumatic Brain Injury", Journal of Neurotrauma, 17(10): 927-938, Oct. 2000.

Rankin et al. "The Therapeutic Effects of An Engineered Human Anti-Tumour Necrosis Factor Alpha Antibody (CDP571) in Rheumatoid Arthritis", British Journal of Rheumatology, 34(4): 334-342, Apr. 1995.

(56) References Cited

OTHER PUBLICATIONS

Roberts et al. "RNA-Peptide Fusions for the In Vitro Selection of Peptides and Proteins", Proc. Natl. Acad. Sci. USA, 94(23): 12297-12302, Nov. 11, 1997.
Rudikoff et al. "Single Amino Acid Substitution Altering Antigen-Binding Specificity", Proc. Natl. Acad. Sci. USA, 79: 1979-1983, Mar. 1982.
Scott et al. "Searching for Peptide Ligands With An Epitope Library", Science, New Series, 249(4967): 386-390, Jul. 27, 1990.
Shohami et al. "Cytokine Production in the Brain Following Closed Head Injury: Dexanabinol (HU-211) Is A Novel TNF-Alpha Inhibitor and An Effective Neuroprotectant", Journal of Neuroimmunology, 72(2): 169-177, Feb. 1997.
Stack et al. "Randomised Controlled Trial of CDP571 Antibody to Tumour Necrosis Factor-Alpha in Crohn's Disease", The Lancet, 349(9051): 521-524, Feb. 22, 1997.
Steinacker et al. "Neuroprotective Function of Cellular Prion Protein in A Mouse Model of Amyotrophic Lateral Sclerosis", The American Journal of Pathology, XP055175444, 176(3): 1409-1420, Mar. 2010. pAkt Is Increase at Final Disease in AML Mice, p. 1416, r-h Col.
Takasaki et al. "Structure-Based Design and Characterization of Exocyclic Peptidomimetics That Inhibit TNF Alpha Binding to Its Receptor", Nature Biotechnology, 15(12): 1266-1270, Nov. 1997.
Thompson "Apoptosis in the Pathogenesis and Treatment of Disease", Science, New Series, 267(5203): 1456-1462, Mar. 10, 1995.
Treon et al. "Interleukin-6 in Multiple Myeloma and Related Plasma Cell Dyscrasias", Current Opinion in Hematology, 5(1): 42-48, Jan. 1998.
Van Regenmortel et al. "D-Peptides as Immunogens and Diagnostic Reagents", Current Opinion in Biotechnology, 9(4): 377-382, Aug. 1998.
Venderova et al. "Programmed CeU Death in Parkinson's Disease", Cold Spring Harbor Perspective in Medivene, p. 1-23, 2012.
Wagey et al. "Phosphatidylinositol 3-Kinase: Increased Activity and Protein Level in Amyotrophic Lateral Sclerosis", Journal of Neurochemistry, 71(2): 716-722, Aug. 1998.
Wang et al. "Tumor Associated Antigen (TAA) Mimicry and Immunotherapy of Malignant Diseases From Anti-Idiotypic Antibodies to Peptide Mimics", Cancer Chemotherapy and Biological Response Modifiers, XP009118039, 19: 309-326, 2001.
Wells et al. "Rapid Evolution of Peptide and Protein Binding Properties In Vitro", Current Opinion in Biotechnology, 3(4): 355-362, Aug. 1992.
Wilson et al. "Phage Display: Applications, Innovations, and Issues in Phage and Host Biology", Canadian Journal of Microbiology, 44(4): 313-329, Apr. 1998.
Wolf et al. "Reconstitution of p53 Expression in A Nonproducer Ab-MuLV-Transformed Cell Line by Transfection of A Functional p53 Gene", Cell, 38(1): 119-126, Aug. 1984.
Yonish-Rouach et al. "Wild-Type p53 Induces Apoptosis of Myeloid Leukaemic Cells That Is Inhibited by Interleukin-6", Nature, 352(6333): 345-347, Jul. 25, 1991.
Zhang et al. "Inhibition of P53 After Acute Myocardial Infarction: Reduction of Apoptosis is Counteracted by Disturbed Scar Formation and Cardiac Rupture", Journal of Molecular and Cellular Cardiology 50(3): 471-478, Mar. 31, 2011.
Zheng et al. "Tumor Suppressor P53 Inhibits Autoimmune Inflammation and Macrophage Function", Diabetes, 54: 1423-1428, May 2005.
Zhou et al. "Akt Regulates Cell Survival and Apoptosis at A Postmitochondrial Level", The Journal of Cell Biology, 151(3): 483-494, Published Online Oct. 30, 2000.

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial sequence
<220> FEATURE:
<223> OTHER INFORMATION: Stressin-1 synthetic peptide
<220> FEATURE:
<221> NAME/KEY: misc_feature
<222> LOCATION: (1)..(7)
<223> OTHER INFORMATION: D stereo isomer

<400> SEQUENCE: 1

Leu Pro Pro Leu Pro Tyr Pro
1               5

<210> SEQ ID NO 2
<211> LENGTH: 7
<212> TYPE: PRT
<213> ORGANISM: Artificial sequence
<220> FEATURE:
<223> OTHER INFORMATION: Stressin-1 sequence reversed synthetic peptide

<400> SEQUENCE: 2

Pro Tyr Pro Leu Pro Pro Leu
1               5
```

USE OF AKT PHOSPHORYLATION AS A BIOMARKER FOR PROGNOSING NEURODEGENERATIVE DISEASES AND TREATING SAME

RELATED APPLICATIONS

This application is a division of U.S. patent application Ser. No. 16/352,879 filed on Mar. 14, 2019, which is a division of U.S. patent application Ser. No. 14/883,685 filed on Oct. 15, 2015, now U.S. Pat. No. 10,288,622, which is a division of U.S. patent application Ser. No. 14/119,891 filed on Nov. 25, 2013, which is a National Phase of PCT Patent Application No. PCT/IL2012/050185 having International Filing Date of May 23, 2012, which claims the benefit of priority under 35 USC § 119(e) of U.S. Provisional Patent Application No. 61/488,806 filed on May 23, 2011. The contents of the above applications are all incorporated by reference as if fully set forth herein in their entirety.

SEQUENCE LISTING STATEMENT

The ASCII file, entitled 85195SequenceListing.txt, created on Oct. 27, 2020 comprising 909 bytes, submitted concurrently with the filing of this application is incorporated herein by reference.

FIELD AND BACKGROUND OF THE INVENTION

The present invention relates to uses of a AKT activating agents for the treatment of neurodegenerative diseases, such as amyotrophic lateral sclerosis (ALS). The present invention relates to uses of a peptide comprising an amino acid sequence selected from the group consisting of SEQ ID NO: 1, SEQ ID NO: 2, analogues and derivatives thereof, for the treatment of neurodegenerative diseases, such as amyotrophic lateral sclerosis (ALS). The present invention further provides a method for assessing responsiveness to treatment with the peptide of the invention. In addition, the present invention relates to prognosis of neurodegenerative diseases, such as ALS progression, using Akt and phosphorylated Akt as biomarkers.

The serine/threonine protein kinase Akt, also known as protein kinase B (PKB) or RAC-PK, was initially identified as one of the downstream targets of phosphatidylinositol-3 kinase (PI3K). Activated Akt plays a key role in mediating signals for cell growth, cell survival (anti-apoptotic), cell-cycle progression, differentiation, transcription, translation and glucose metabolism.

The Akt pathway is damaged in skeletal muscles of amyotrophic lateral sclerosis (ALS) patients, as in SOD1 mice (a mice model for ALS). Although no difference in Akt mRNA levels is found in ALS patients when compared to control subjects, at the protein level, ALS patients, have a significantly lower content of the active phosphorylated Akt protein in comparison to healthy control subjects (Leger et al., FASEB J. 2006; 20(3):583-585). Akt pathway dysfunction has also been shown in motoneurons of both sporadic and familial ALS patients (Dewil et al., Neuropathol Appl Neurobiol., 2007; 33(5):499-509).

The peptides LPPLPYP (SEQ ID NO: 1; also known as Stressin-1) and PYPLPPL (SEQ ID NO: 2, where all residues are in the "D" isomeric form) were first disclosed in WO 2006/021954, where their efficacy in ameliorating stress-induced cell death and p53-mediated response was demonstrated. According to the disclosure, these peptides are also useful in treating inflammatory and autoimmune diseases. Nowhere in the background art was it taught or suggested that the activity of peptides comprising SEQ ID NO: 1 or SEQ ID NO: 2 or derivatives thereof is affected by the level of Akt and Akt phosphorylation, such that, the therapeutic effect of these peptides would be significantly higher in subjects having low levels of pAkt and, optionally, low levels of pAkt:tAkt ratio. In addition, the background art does not teach or even suggests the use of pAkt and pAkt:tAkt ratio as effective markers for ALS and moreover for staging the progression of ALS in ALS patients.

ALS is a devastating and rapidly fatal disease with currently only one available, FDA-approved, modestly effective treatment. The approve therapy, Rilutek® (Riluzole), has a modest benefit estimated to be a three month extension in patient survival.

There is therefore an urgent need for new therapies. Recent attempts to find molecules that could provide a beneficial therapy for ALS include the finding of 1,4-Diazabicyclo[3.2.2]non-6-en-4-yl)-heterocyclyl-methanone ligands disclosed in US Patent Application, Publication No. 2010/0298306. The ligands are directed to treatment of any Nicotinic Acetylcholine Receptors, inter alia, ALS. In addition, US Patent Application, Publication No. 2010/0099700, discloses use of hydrogenated pyrido(4,3-b)indole for treating ALS. US Patent Application, Publication No. 2009/0324549 discloses methods for treating ALS comprising administration to a patient in need thereof, proteins and/or peptides characterized in that they originate from the gene which results from the retention of the intron 3 of the gene SMN (or survival motor neuron) identified in the gene bank with the access number AY876898.

WO 2011/017030 discloses a method of treating a disease associated with excess activation of monocytes to activated macrophages, including, inter alia, ALS said method comprising administering a therapeutically-effective amount of an oxidative agent to a subject in need thereof, wherein said oxidative agent is selected from the group consisting of non-halogen activated-oxygen compounds, non-oxygen activated-halogen compounds, and N-halo compounds. According to WO 2011/017030 the non-halogen activated-oxygen compounds are selected from potassium nitrate ($KNO_3$), permanganate salts, ammonium cerium(IV) nitrate, hexavalent chromium compounds, chromate/dichromate compounds, ammonium silver nitrate, sulfoxides, persulfuric acid, osmium tetroxide ($OsO_4$), nitric acid, nitrous oxide ($N_2O$), hydrogen peroxide, organic peroxides, superoxides, and ozone; the non-oxygen activated-halogen compounds are selected from fluorine, chlorine, bromine, and iodine; the N-halo compounds are selected from the group consisting of N-halophthalimide, N-halosuccinimide, N-halosaccharin, N,N-dihalourethane, N-haloacetanilide, 1,3-dihalo-5,5-dimethylhydantoin, trihaloisocyanuric acid and sodium dihaloisocyanurate; and the oxidative agent is selected from 1,3-dichloro-5,5-dimethylhydantoin and chloramine-T.

The development of the first genetically based mouse model of ALS in 1994, energized the field of preclinical testing despite numerous unforeseen complexities along the way. Transgenic mutant SOD1 mice, the only ALS mouse models currently available, have mutations in the Cu/Zn Superoxide Dismutase 1 gene (SOD1) which account for ~20% of Familial ALS (FALS) cases, corresponding to 2-3% of all ALS cases. Transgenic mutant SOD1 mice exhibit all of the histopathological hallmarks observed clinically in sporadic and familial ALS.

Because there is no obvious mutational hotspot and no clear correlation between the level of enzymatic activity of the mutant SOD1 protein and the observed disease phenotype or clinical progression, SOD1 is thought to act primarily via a toxic gain of function in ALS, although loss of function may also contribute to disease pathophysiology. It is generally thought that the different mutant SOD1 proteins are likely to cause ALS by a similar mechanism.

Several transgenic mouse models have been generated to model mutations found in FALS patients. In all of these mouse models, massive death of motor neurons in the ventral horn of the spinal cord and loss of myelinated axons in ventral motor roots ultimately leads to paralysis and muscle atrophy. All of these mouse models have been reported to exhibit the same histopathological hallmarks associated with ALS in humans: progressive accumulation of detergent-resistant aggregates containing SOD1 and ubiquitin and aberrant neurofilament accumulations in degenerating motor neurons. In addition to neuronal degeneration, reactive astroglia and microglia have also been detected in diseased tissue in the mice, similar to that observed in humans.

Despite these histopathological similarities, the timing of onset and rate of disease progression differ (often dramatically) among the various SOD1 transgenic mouse models.

ALS is commonly assessed by neurological score and weight loss. As used herein, the term "neurological score" and "neurologic score" are interchangeably used herein to describe the common standards for assessing the presence or stage of a neurologic disease, such as ALS. Some example of commonly used neurological scoring systems include: measurements of splay (or other measures of paralysis) and beam walk.

In SOD1 mice, regardless of which neurological scoring system is used, scores are typically assessed for both hind legs of the SOD1 mice. The example neurological scoring system below employs a scale of zero to four (www(dot)researchals(dot)org/uploaded_files/
p41_jax_sod1manual_20091202_29aPcx(dot)pdf).
Example of score criteria used to assign each score under this system are as follows:
Score of 0: full extension of hind legs away from lateral midline when mouse is suspended by its tail, and mouse can hold this for two seconds, suspended two to three times.
Score of 1: collapse or partial collapse of leg extension towards lateral midline (weakness) or trembling of hind legs during tail suspension.
Score of 2: toes curl under at least twice during walking of 12 inches, or any part of foot is dragging along cage bottom/table.
Score of 3: rigid paralysis or minimal joint movement, foot not being used for generating forward motion.
Score of 4: mouse cannot right itself within 30 seconds after being placed on either side.

U.S. Pat. No. 7,659,243 discloses the use of angiogenin, or a fragment or variant thereof, to treat diseases characterized by neuronal injury or death, or axonal degeneration, especially neurodegenerative diseases such as ALS. According to the disclosure, the neuroprotective effect of angiogenin involves the activation of the PI3K/Akt pathway.

U.S. Pat. Nos. 7,030,090 and 7,517,857 disclose a peptide that stimulates Akt phosphorylation via activation of formyl peptide receptor or formyl peptide receptor-like 1, the peptide comprises an amino acid sequence of WX1X2MX3X4, where X1=K, R, E, H or D, X2=G, Y, H, E or W, X3=V or G and X4=D-Me or G.

U.S. Pat. No. 7,622,455 discloses a method of treating ALS comprising administering to the cerebrospinal fluid of a subject in need thereof antisense oligonucleotides complementary to SOD1 nucleic acids.

There is an unmet need for novel methods for slowing down the rate of progression of neurodegenerative diseases, such as ALS, assessing responsiveness to treatment of the disease, and staging the disease in a manner that is specific, safe and effective.

SUMMARY OF THE INVENTION

The present invention provides methods for treating neurodegenerative diseases, such as ALS and variants of this disease, the method comprises assessing pAkt level and the level of ratio pAkt to total Akt (tAkt) in a subject in need thereof, followed by administering to a subject having pAkt and/or pAkt:tAkt ratio significantly below a predetermined threshold level, a composition comprising a peptide having an amino acid sequence comprising a sequence selected from the group consisting of SEQ ID NO: 1 and SEQ ID NO: 2.

While use of the peptides of the invention for ameliorating stress-induced cell death and p53-mediated response has been described, the present invention demonstrates that said peptides are useful in increasing the levels of Akt phosphorylation, thereby better defining the population that would benefit from treatment with the peptide.

It is now disclosed for the first time that a peptide having an amino acid sequence consisting of SEQ ID NO: 1 or SEQ ID NO:2 activates the Akt pathway. The peptide-induced activation of the Akt pathway in a specific manner was detected shortly after introducing said peptide to macrophages culture. The peptide's induced activation of the Akt pathway was also observed in vivo. Thereby, the invention demonstrates that the peptides of the invention are useful for treating diseases associated with low Akt phosphorylation (pAkt) or low pAkt:tAkt ratio.

Surprisingly, administering the peptide of the invention to SOD1 mice enhanced survival and prolonged the life span of said mice in a significant manner (10 days longer; P=0.008) in comparison to non-treated mice. In addition to extended survival, the peptide of the invention significantly delays disease progression by delaying the appearance of the disease symptoms, primarily, the challenged mobility.

Without wishing to be bound by theory or mechanism, the advantages of the peptide of the invention over other treatments of ALS known to date may be attributed to the fact that the peptide was tested, and shown to be effective not only before disease onset but also after disease onset including at very late stage of disease.

Advantageously, use of the peptide of the invention is relatively safe, as administration of the peptide in a dose that is four times higher than the effective dose, daily, for 28 days, did not initiate any detectable side effect in healthy mice. Accordingly, the peptide of the invention is suitable for chronic use. In addition, the peptide of the invention was shown effective when administered intravenously (IV), intraperitoneally (IP) or in combination of these two modes of delivery.

The present invention also highlights the use of Akt phosphorylation and pAkt:tAkt ratio as biomarkers that are significantly useful for staging and monitoring the progression of ALS. Based on the teaching of the present invention, Akt phosphorylation and pAkt:tAkt ratio distinguish between fast progression to low progression of ALS. Specifically, low Akt phosphorylation and, optionally, low pAkt:tAkt ratio indicate rapidly progressing ALS whereas high levels of Akt phosphorylation and, optionally, high pAkt:

tAkt ratio indicate slow progression of the disease. The biomarkers of the invention are also useful for establishing responsiveness to treatment with the peptides of the invention. It is shown that high levels of pAkt and high levels of pAkt:tAkt ratio (e.g. above 1) correlate with responsiveness to treatment of ALS with the peptides of the invention.

According to an aspect of some embodiments of the present invention there is provided a method for prognosticating the progression of a neurodegenerative disease in a subject, comprising (a) assessing the value of at least one marker selected from: pAkt and pAkt:tAkt ratio, in a bodily sample derived from the subject; and (b) obtaining the ratio between the value of the marker and the value of the marker in a control sample, wherein a level of pAkt or pAkt:tAkt ratio significantly below a control value indicates a rapid disease.

According to an aspect of some embodiments of the present invention there is provided a method for treating a neurodegenerative disease in a subject in need thereof, comprising administering to a subject having a rapidly progressing neurodegenerative disease a therapeutically effective amount of an agent capable of activating a Akt pathway, thereby treating the neurodegenerative disease.

According to an aspect of some embodiments of the present invention there is provided a method for treating a neurodegenerative disease in a subject in need thereof, comprising (a) assessing the level of pAkt and pAkt:tAkt ratio in a bodily sample derived from the subject; and (b) administering a therapeutically effective amount of a peptide comprising an amino acid sequence selected from the group consisting of SEQ ID NO: 1, SEQ ID NO: 2 and an analog or a derivative thereof, to a subject having pAkt level or pAkt:tAkt ratio significantly below a control value.

According to an aspect of some embodiments of the present invention there is provided a method for treating amyotrophic lateral sclerosis (ALS) in a subject in need thereof, comprising (a) assessing the level of pAkt and pAkt:tAkt ratio in bodily sample derived from the subject; and (b) administering a therapeutically effective amount of a peptide comprising an amino acid sequence selected from the group consisting of SEQ ID NO: 1, SEQ ID NO: 2 and an analog or a derivative thereof, to a subject having pAkt level or pAkt:tAkt ratio significantly below a control value.

According to an aspect of some embodiments of the present invention there is provided a method for assessing responsiveness to treatment of a disease with a peptide comprising an amino acid sequence of SEQ ID NO: 1, SEQ ID NO: 2 or an analog or a derivative thereof, or a pharmaceutical composition comprising same, the method comprising: assessing the level of pAkt or pAkt:tAkt ratio in bodily sample derived from a subject, wherein responsiveness to treatment is indicated by a pAkt level or pAkt:tAkt ratio significantly above a value of a pAkt level or pAkt:tAkt ratio in the subject prior to the treatment.

According to an aspect of some embodiments of the present invention there is provided a kit for diagnosing a neurodegenerative disease or prognosticating its progression in a subject comprising i) means for collecting a bodily sample from a subject and ii) means for determining the level of pAkt and tAkt in the sample.

According to an aspect of some embodiments of the present invention there is provided a method of determining the efficacy of treatment of a neurodegenerative disease in a subject in need thereof comprising determining in a sample from the subject the effect of a peptide comprising an amino acid sequence selected from the group consisting of SEQ ID NO: 1, SEQ ID NO: 2 on the level of pAkt and pAkt:tAkt ratio, wherein an increase in the level indicates that the subject is responsive to treatment with the peptide.

According to some embodiments of the invention, the disease is selected from the group consisting of: amyotrophic lateral sclerosis (ALS), primary lateral sclerosis (PLS) and spinal muscular atrophy (SMA).

According to some embodiments of the invention, the disease is amyotrophic lateral sclerosis (ALS).

According to some embodiments of the invention, the disease is selected from the group consisting of: Alzheimer's disease, Parkinson's disease, glaucoma, macular degeneration, hypoxia, fulminant toxic liver, kidney failure and infertility.

According to some embodiments of the invention, the bodily sample is selected from the group consisting of: muscle, blood, blood plasma, lymph fluid, lymphocytes and leukocytes.

According to some embodiments of the invention, the control value corresponds to pAkt level or pAkt:tAkt ratio in a sample selected from the group consisting of: a bodily sample of a healthy individual, a bodily sample of an individual not afflicted with any neurodegenerative disease, a bodily sample of an individual afflicted with a slowly progressing neurodegenerative disease and a sample derived from an ALS subject having a slow disease.

According to some embodiments of the invention, the agent capable of activating the Akt pathway comprises a peptide comprising an amino acid sequence selected from the group consisting of SEQ ID NO: 1, SEQ ID NO: 2 and an analog or a derivative thereof.

According to some embodiments of the invention, the agent capable of activating the Akt pathway is selected from the group consisting of a insulin-like growth factor 1 (IGF-I), vascular endothelial growth factor (VEGF), angiogenin, naphtho[1,2-b]furan-4,5-dione (NFD), ciliary neurotrophic factor (CNTF), brain-derived neurotrophic factor (BDNF), growth factor-beta (TGF-beta), glial-cell-line-derived neurotrophic factor (GDNF), Hepatic growth factor (HGF), fibroblast growth factor (FGF) and epidermal growth factor (EGF).

According to some embodiments of the invention, the agent capable of activating the Akt pathway is administered by a route of administration selected from the group consisting of: oral, transdermal, parenteral, transmucosal, intrathecal, intracerebroventricular (ICV), intranasal, sublingual, intravenous and intraperitoneal.

According to some embodiments of the invention, determining a progression of the neurodegenerative disease is effected according to the method of the present invention.

According to some embodiments of the invention, the bodily sample is derived from the peripheral blood, the lymph system or a muscle of the subject.

According to some embodiments of the invention, the peripheral blood or the lymph system comprises lymphocytes.

According to some embodiments of the invention, the peptide is comprised in a pharmaceutical composition in combination with at least one more therapeutic drug.

According to some embodiments of the invention, the at least one more therapeutic drug is selected from the group consisting of: an oxidative agent, non-halogen activated-oxygen compounds, non-oxygen activated-halogen compounds, N-halo compounds and riluzole.

According to some embodiments of the invention, the pharmaceutical composition further comprises a pharmaceutical acceptable excipient, carrier or diluent.

According to some embodiments of the invention, treating comprises attenuating the progression of the disease, alleviating symptoms of the disease, delaying the appearance of disease symptoms or improving management of the disease.

According to some embodiments of the invention, administering the peptide by a route of administration selected from the group consisting of: oral, transdermal, parenteral, transmucosal, intrathecal, intracerebroventricular (ICV), intranasal, sublingual, intravenous and intraperitoneal.

According to some embodiments of the invention, the peptide consists of an amino acid sequence selected from SEQ ID NO: 1, SEQ ID NO: 2 and an analog or a derivative thereof.

According to some embodiments of the invention, the bodily sample is derived from the peripheral blood, the lymph system or the muscle of the subject.

According to some embodiments of the invention, the peripheral blood or the lymph system comprises lymphocytes.

According to some embodiments of the invention, treating comprises administering the peptide by a route of administration selected from the group consisting of: oral, transdermal, parenteral, transmucosal, intrathecal, intracerebroventricular (ICV), intranasal, sublingual, intravenous and intraperitoneal.

According to some embodiments of the invention, the kit further comprises a standard, a calibration curve or an index indicating a control value of the pAkt and the tAkt.

According to some embodiments of the invention, the control value corresponds to pAkt level or pAkt:tAkt ratio in a sample selected from the group consisting of: a bodily sample of a healthy individual, a bodily sample of an individual not afflicted with any neurodegenerative disease, a bodily sample of an individual afflicted with a slowly progressing neurodegenerative disease and a sample derived from a subject having a slow disease.

According to some embodiments of the invention, the means for determining the levels of pAkt comprise at least one antibody directed to pAkt.

According to some embodiments of the invention, the means for determining the levels of tAkt comprise at least one antibody directed to tAkt.

These and other embodiments of the present invention will become apparent in conjunction with the figures, description and claims that follow.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
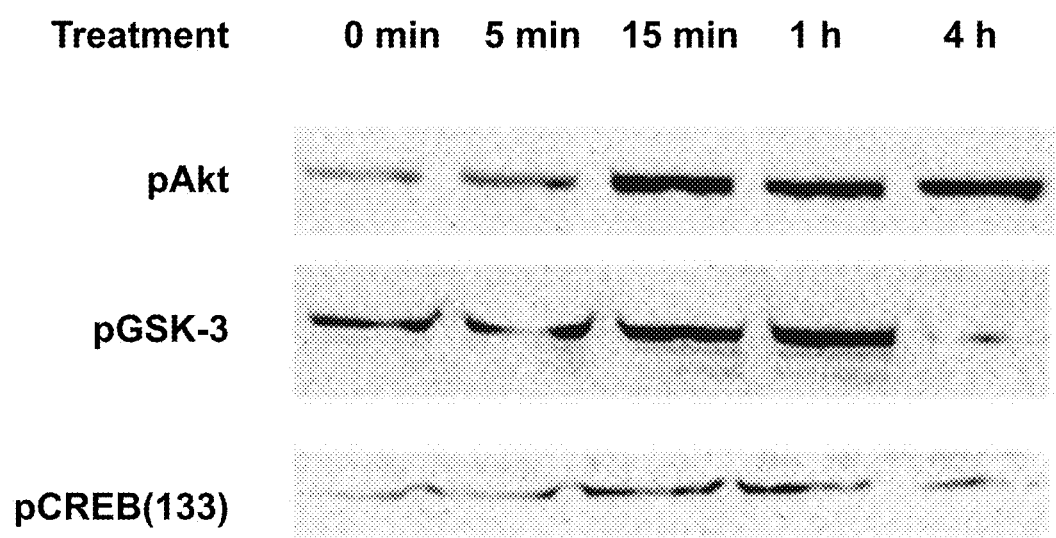
FIG. 1A presents Akt phosphorylation in macrophages treated with a peptide having the amino acid sequence of SEQ ID NO: 1.

The present invention provides methods for treating diseases associated with low Akt phosphorylation levels, such as ALS, comprising administering to a subject in need thereof a pharmaceutical composition comprising a peptide comprising an amino acid sequence selected from the group consisting of SEQ ID NO: 1, SEQ ID NO: 2, analogues or derivatives thereof. The present invention also provides methods for assessing responsiveness to treatment of diseases associated with low Akt phosphorylation levels, such as ALS with the peptide of the invention, comprising evaluating the level of Akt phosphorylation and pAkt:tAkt ratio prior to treatment, and comparing the values to a control value, thereby determining responsiveness to therapy with the peptide of the invention.

According to one embodiment, there is provided a method for treating a neurodegenerative disease in a subject in need thereof, comprising administering to a subject having a rapidly progressing neurodegenerative disease a therapeutically effective amount of an agent capable of activating a Akt pathway, thereby treating the neurodegenerative disease.

According to one embodiment, there is provided a method for treating a neurodegenerative disease in a subject in need thereof, comprising (a) assessing the level of pAkt and pAkt:tAkt ratio in a bodily sample derived from the subject; and (b) administering a therapeutically effective amount of a peptide comprising an amino acid sequence selected from the group consisting of SEQ ID NO: 1, SEQ ID NO: 2 and an analog or a derivative thereof, to a subject having pAkt level or pAkt:tAkt ratio significantly below a control value.

The term "treating" as used herein includes prophylactic and therapeutic uses, and refers to the alleviation of symptoms of a particular disease in a patient, and/or improvement of an ascertainable measurement associated with a particular disorder. More specifically, in the context of this invention "treating a disease associated with low levels of Akt phosphorylation", particularly ALS, means attenuating the progression of said disease and/or alleviating symptoms of said disease and/or improving management of said disease. This modulation can be measured by assessing the level of Akt phosphorylation upon treatment and prior to treatment, where assessment of Akt phosphorylation may be carried out in ways which are routine in the art, for example, mass spectroscopy.

As used herein the term "subject" refers to a mammalian subject, e.g. human subject, who is at risk of developing a neurodegenerative disease or who exhibits clinical signs of a neurodegenerative disease. The subject may be of any age and gender.

Examples of neurodegenerative diseases which may be treated according to the present invention include, but are not limited to, Amyotrophic Lateral Sclerosis (ALS), primary lateral sclerosis (PLS), spinal muscular atrophy (SMA), Alzheimer's disease, Parkinson's disease, glaucoma, macular degeneration, hypoxia, fulminant toxic liver, kidney failure, infertility, type 1 diabetes, multiple sclerosis, systemic lupus erythematosis, autoimmune uveitis, graft versus host disease, graft rejection, arthritis, systemic inflammatory response syndrome (SIRS), inflammatory bowel disease (IBD), adult respiratory distress syndrome (ARDS), psoriasis, atherosclerosis.

According to a specific embodiment, the neurodegenerative disease is ALS.

As used herein "amyotrophic lateral sclerosis (ALS)" also referred to as "Lou Gehrig's disease" refers to a progressive, fatal, neurodegenerative disease caused by the degeneration of motor neurons, the nerve cells in the central nervous system that control voluntary muscle movement. The term ALS includes sporadic and familial ALS, ALS at any rate of progression (i.e. rapid or slow progression) and ALS at any stage (e.g. prior to onset, at onset and late stages of ALS).

ALS typically causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. Affected subjects may ultimately lose the ability to initiate and control all voluntary movement; bladder and bowel sphincters and the muscles responsible for eye movement are usually, but not always, spared.

Cognitive function is generally spared except in certain situations such as when ALS is associated with frontotemporal dementia. However, there are reports of more subtle cognitive changes of the frontotemporal type in many patients when detailed neuropsychological testing is employed. Sensory nerves and the autonomic nervous system, which controls functions like sweating, generally remain functional. ALS as used herein refers to all the above exemplary manifestations. ALS, as used herein refers to hereditary and sporadic ALS.

Both hereditary causes and environmental risks may contribute to onset of disease. For instance, an inherited genetic defect on chromosome 21 (coding for superoxide dismutase) is associated with approximately 20% of familial cases of ALS. This mutation is believed to be autosomal dominant. The most common ALS causing SOD1 mutation in North America is A4V, characterized by an exceptionally rapid progression from onset to death. The children of those diagnosed with familial ALS have a higher risk factor for developing the disease; however, those who have close family members diagnosed with sporadic ALS have no greater a risk factor than the general population, suggesting an environmental or other non-genetic cause.

Furthermore, environmental causative factors have been suggested for the increased incidence of ALS. These include, prolonged exposure to a dietary neurotoxin called BMAA produced by cyanobacteria which is one of several possible neurotoxic compounds found in the seed of the cycad *Cycas circinalis*, a tropical plant found in Guam; Exposure to pesticides; toxic exposure such as nerve gas.

As mentioned above, the method of the invention is directed, inter alia, for treating ALS. The treatment may be initiated at any stage of the disease, including following detection of ALS symptoms.

Detection of ALS may be determined by the appearance of different symptoms depending on which motor neurons in the body are damaged first (and consequently which muscles in the body are damaged first). In general, ALS symptoms include the earliest symptoms which are typically obvious weakness and/or muscle atrophy. Other symptoms include muscle fasciculation (twitching), cramping, or stiffness of affected muscles, muscle weakness affecting an arm or a leg and/or slurred and nasal speech. Most ALS patients experience first symptoms in the arms or legs. Others first notice difficulty in speaking clearly or swallowing. Other symptoms include difficulty swallowing, and loss of tongue mobility. A small proportion of patients experience respiratory difficulties.

The symptoms may be also classified by the part of neuronal system that is degenerated, namely, upper motor neurons and lower motor neurons. Symptoms of upper motor neuron degeneration include tight and stiff muscles (spasticity) and exaggerated reflexes (hyperreflexia) including an overactive gag reflex. Symptoms of lower motor neuron degeneration include muscle weakness and atrophy, muscle cramps, and fleeting twitches of muscles that can be seen under the skin (fasciculations). To be diagnosed with ALS, patients must have signs and symptoms of both upper and lower motor neuron damage that cannot be attributed to other causes.

Alternatively, treatment may be initiated at progressive stages of the disease, e.g. when muscle weakness and atrophy spread to different parts of the body and the subject has increasing problems with moving [e.g. the subject may suffer from tight and stiff muscles (spasticity), from exaggerated reflexes (hyperreflexia), from muscle weakness and atrophy, from muscle cramps, and/or from fleeting twitches of muscles that can be seen under the skin (fasciculations)], swallowing (dysphagia), speaking or forming words (dysarthria).

The present invention further provides a method for treating amyotrophic lateral sclerosis (ALS) in a subject in need thereof, the method comprising administering to the subject a therapeutically effective amount of a peptide comprising an amino acid sequence selected from the group consisting of SEQ ID NO: 1, SEQ ID NO: 2 and an analog or a derivative thereof, thereby treating the ALS.

The present invention contemplates treatment using the peptide comprising an amino acid sequence of SEQ ID NO: 1, SEQ ID NO: 2 or an analog or a derivative thereof.

The present invention encompasses any analog, derivative, and conjugate containing the peptides of the invention, the amino acid sequence of which is shown herein so long as the peptide is capable of inducing Akt phosphorylation. Thus, the present invention encompasses peptides containing non-natural amino acid derivatives or non-protein side chains.

The term "analog" includes any peptide or polypeptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

A peptide derivative refers to a molecule comprising the amino acid sequence of a peptide of the invention subject to various changes, including, but not limited to, chemical modifications, substitutions, insertions, extensions and deletions where such changes do not destroy the anti-inflammatory or anti-apoptotic activity of the peptide, and such derivative is not a known peptide or protein. "Peptide derivative" is intended to include peptide mimetics, as described hereinbelow.

Peptide derivatives having chemical modifications include, for example, peptides having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH$_2$ acylation, acetylation, or thioglycolic acid amidation, and by terminal-carboxyl-amidation, e.g., with ammonia, methylamine, and the like.

Preferred peptide derivatives are retro-inverso peptides. In particular embodiment the methods of the invention provides uses of a peptide having the amino acid sequence set forth in SEQ ID NO: 1 or a retro-inverso derivative thereof as set forth in SEQ ID NO: 2.

As used herein, the term "retro-inverso peptide" of the peptide of SEQ ID NO: 1, for example, as used in a variation of the invention, is intended to encompass peptides in which the sequence of the amino acids is reversed as compared to the sequence in SEQ ID NO: 1 and consist of D-amino acids in reversed order. Retro-inverso peptides consist of D-amino acids in reversed order, resulting in an altered peptide backbone but unchanged orientation of the side chains. Retro-inverso peptides are usually advantageous over the original peptide as they are resistant to proteases.

Peptides of the present invention also include any peptide having one or more additions and/or deletions of residues relative to the sequence of the peptides of the invention, the sequence of which are shown herein, so long as the requisite induction activity of Akt phosphorylation is maintained.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

A peptide of the invention may also be conjugated to itself or aggregated in such a way as to produce a large complex containing the peptide. Such large complex may be advantageous because it has new biological properties such as longer half-life in circulation or greater activity.

Peptidomimetics are small molecules that can bind to proteins by mimicking certain structural aspects of peptides and proteins. They are used extensively in science and medicine as agonists and antagonists of protein and peptide ligands of cellular and other receptors, and as substrates and substrate analogs for enzymes.

A primary goal in the design of peptide mimetics has been to reduce the susceptibility of mimics to cleavage and inactivation by peptidases. In one approach, one or more amide bonds have been replaced in an essentially isosteric manner by a variety of chemical functional groups, including, but not limited to urea bond, carbamate bond, sulfonamide bond, hydrazine bond, or any other covalent bond. In another approach, a variety of uncoded or modified amino acids such as D-amino acids and N-methyl amino acids have been used to modify mammalian peptides.

As mentioned, treating the neurodegenerative disease may be affected by administration of a therapeutically effective amount of an agent capable of activating a Akt pathway.

As used herein, the phrase "agent capable of activating a Akt pathway" refers to a molecule that upregulates phosphorylation of Akt per se or a down-stream signaling effector thereof (i.e., indirect activation).

Any agent capable of activating a Akt pathway may be used in accordance with the present teachings. Exemplary agents which may used include, but are not limited to, insulin-like growth factor 1 (IGF-I), vascular endothelial growth factor (VEGF), angiogenin, naphtho[1,2-b]furan-4,5-dione (NFD), ciliary neurotrophic factor (CNTF), brain-derived neurotrophic factor (BDNF), growth factor-beta (TGF-beta), glial-cell-line-derived neurotrophic factor (GDNF), Hepatic growth factor (HGF), fibroblast growth factor (FGF) and epidermal growth factor (EGF).

Each of the agents capable of activating a Akt pathway or the peptide comprising an amino acid sequence of SEQ ID NO: 1, SEQ ID NO: 2 or an analog or a derivative thereof as described hereinabove can be administered to the subject per se or as part of a pharmaceutical composition.

As used herein a "pharmaceutical composition" refers to a preparation comprising the peptide of the invention, with other chemical components such as physiologically suitable carriers and excipients. The purpose of a pharmaceutical composition is to facilitate administration of a compound to a patient in need thereof.

The composition of the invention may be administered by any conventional and appropriate route of administration, including, but not limited to, oral, intravenous, intramuscular, subcutaneous, intrathecal, topical, rectal, buccal, inhalational, intranasal transdermal, parenteral, transmucosal, sublingual, intravenous and intraperitoneal.

Hereinafter, the term "oral administration" includes, but is not limited to, administration by mouth for absorption through the gastrointestinal tract (peroral) wherein the drug is swallowed, or for trans-mucosal absorption in the oral cavity by buccal, gingival, lingual, sublingual and oropharyngeal administration. Compositions for oral administration include powders or granules, suspensions or solutions in water or non-aqueous media, sachets, capsules or tablets. The oral composition can optionally contain inert pharmaceutical excipients such as thickeners, diluents, flavorings, dispersing aids, emulsifiers, binders, preservatives and the like.

The term "parenteral administration" as used herein indicates any route of administration other than via oral administration and includes, but is not limited to, administration by intravenous drip (IV) or bolus injection, intraperitoneal (IP), intrathecal, subcutaneous, or intra muscular injection, topical, transdermal, rectal, intranasal (IN) administration or by inhalation.

According to one embodiment, the peptide as set forth in SEQ ID NO: 1, SEQ ID NO: 2 and an analog or a derivative thereof is administered via a combination of two routes (e.g. intraperitoneal and intravenous routes).

According to one embodiment, the peptide of the invention is administered orally.

Formulations for parenteral administration include but are not limited to sterile aqueous solutions which can also contain buffers, diluents and other suitable additives.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

For administration by inhalation, the peptides for use according to the present invention are conveniently delivered in the form of an aerosol spray presentation from a pressurized pack or a nebulizer with the use of a suitable propellant, e. g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

The pharmaceutical compositions of the invention are also useful for topical application. As used herein, the term "topical" means "pertaining to a particular surface area", e.g. skin and mucosa, and the topical agent applied to a certain area of said surface will affect only the area to which it is applied. The formulations of the peptides/peptide analogs may be administered topically as a gel, ointment, cream, emulsion, sustained release formulation including a transdermal patch, and may comprise liposomes and any other pharmaceutically acceptable carrier suitable for administration of the drug topically. The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

The preparation of pharmaceutical compositions which contain peptides or polypeptides as active ingredients is well known in the art. Typically, such compositions are prepared as indictable, either as liquid solutions or suspensions, however, solid forms, which can be suspended or solubilized prior to injection, can also be prepared. The preparation can also be emulsified. The active therapeutic ingredient is mixed with inorganic and/or organic carriers, which are pharmaceutically acceptable and compatible with the active ingredient. Carriers are pharmaceutically acceptable excipients (vehicles) comprising more or less inert substances when added to a pharmaceutical composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents, which enhance the effectiveness of the active ingredient.

Toxicity and therapeutic efficacy of the peptides described herein can be determined by standard pharmaceutical procedures in cell cultures or experimental animals, e. g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compounds or active agents in a single composition or may contain a divided pharmacologically, biologically, therapeutically, or chemically effective amount. The total effective amount can then be administered in cumulative units containing, in total, an effective amount of the active agent.

A therapeutically effective amount of a peptide of the invention is an amount that when administered to a patient for treating a neurodegenerative disease, is capable of attenuating the progression of said disease, alleviating symptoms of said disease and improving management of said disease.

Although an appropriate dosage of a peptide of the invention varies depending on the administration route, age, body weight, sex or conditions of the patient, and should be determined by the physician in the end, the dose suitable for adult humans can generally be between about 0.2-2000 mg/kg body weight, about 0.2-1500 mg/kg body weight, about 0.2-1000 mg/kg body weight, about 0.2-500 mg/kg body weight, about 0.2-200 mg/kg body weight, about 0.2-100 mg/kg body weight, about 1-2000 mg/kg body weight, about 1-1500 mg/kg body weight, about 1-1000 mg/kg body weight, about 1-500 mg/kg body weight, about 1-100 mg/kg body weight, or preferably between about 1-200 mg/kg.

The pharmaceutical compositions of the present invention comprise one or more compounds of the present invention, and one or more excipients, carriers or diluents.

Carriers are pharmaceutically acceptable vehicles comprising more or less inert substances when added to a pharmaceutical composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents, which enhance the effectiveness of the active ingredient.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

The present invention further contemplates administration of other therapeutic drugs to the subject. Exemplary drugs which may be administered include, but are not limited to, oxidative agents, non-halogen activated-oxygen compounds, non-oxygen activated-halogen compounds, N-halo compounds and riluzole.

As mentioned above, in accordance with the present invention, the level of Akt phosphorylation (pAkt) and pAkt:tAkt ratio may be assessed.

As used herein, the term "Akt" refers to the serine/threonine-specific protein kinase also known as Protein Kinase B (PKB). Three genes in the Akt family, in humans: Akt1 (also called Akt), Akt2, and Akt3, encode for enzymes that are members of this serine/threonine-specific protein kinase family. Akt1 is involved in cellular survival pathways, by inhibiting apoptotic processes and is able to induce protein synthesis pathways, which renders it a key signaling protein in the cellular pathways that lead to skeletal muscle hypertrophy, and general tissue growth. Since it can block apoptosis, and thereby promote cell survival, Akt1 has been implicated as a major factor in many types of cancer. Akt2 is an important signaling molecule in the Insulin signaling pathway and is required to induce glucose transport. The role of Akt3 is less clear, though it appears to be predominantly expressed in brain.

As used herein, the term "pAkt" refers to the phosphorylated form of Akt. According to exemplary embodiments, the Akt is phosphorylated on serine and/or threonine site(s), such as serine 308 and threonine 473.

As used herein, the term "pAkt:tAkt ratio" refers to the level of phosphorylated Akt divided by the level of total Akt in the cell or biological sample.

Phosphorylation is probably the most common of protein post translational modifications (PTMs), with 30% of eukaryotic proteins estimated to be modified this way. Phosphorylation is essential to the cell by playing a central role in signal transduction cascades, regulation of protein activity and protein-protein interactions. Protein phosphorylation can be detected as a mass shift (+79.99 Da) in mass spectra, which corresponds to the addition of $HPO_3$ to a peptide, generally at serine, threonine or tyrosine residues.

Methods for measuring protein and peptide phosphorylation (i.e. pAkt) are known in the art and include Kinase Activity Assays, Western blots (i.e. with an anti-pAkt antibody) or Enzyme-Linked Immunosorbent Assays (ELISA, i.e. with an anti-pAkt antibody) and Mass Spectrometry (e.g. Donahue et al., Methods in Enzymology, Volume 434, p. 131-150). Similarly, total Akt (tAkt) levels may be assed using e.g. Western blot (i.e. with an anti-Akt antibody) or Enzyme-Linked Immunosorbent Assay (ELISA i.e. with an anti-Akt antibody).

Without being bound by any theory or mechanism, Akt pathway dysfunction in ALS patients may result from multiple effects of the underlying ALS disease process. Akt is the major signaling pathway activated by at least four major factors and hormones: GH, IGF1, HGF and VEGF. Akt pathway induction by all four is impaired in ALS:

i. GH levels are drastically reduced as a direct result of oxidative stress and other primary disease processes of ALS.

ii. The IGF1 signaling pathway, a major fallback option of GH, is disturbed by up-regulation of IGFBP1 and direct carbonylation damage to the IGF1 Receptor.

iii. Later in the disease, IGF1, HGF and VEGF levels are also decreased, further reducing the natural stress response of the neuro-musculature system.

As shown in Examples 4 and 5 of the Examples section which follows, the present inventors have shown that pAkt correlates with the state of the disease, i.e. in rapidly progressing ALS disease the ratio of muscle/lymph pAkt is significantly lower compared to slow progressing ALS disease. Moreover, the present inventors have shown that pAkt can be used to assess responsiveness to treatment, i.e. when the subject responds to treatment, there is a significant elevation in pAkt levels.

Assessing the level of pAkt or pAkt:tAkt ratio may thus be carried out prior to treatment, upon treatment and following treatment and may be used for various applications as specified in further detail below.

According to one embodiment, there is provided a method of assessing responsiveness to treatment of a disease (e.g. ALS) with the peptide of the present invention, the method comprising: assessing the level of pAkt and pAkt:tAkt ratio in bodily sample, such as, a bodily sample derived from the muscle, the blood or lymphatic system of the subject (e.g. comprising lymphocytes), wherein responsiveness to treatment is indicated by a pAkt level or pAkt:tAkt ratio which is significantly above a value of pAkt level and pAkt:tAkt ratio in the subject prior to the treatment.

As used herein, the terms "above" or "increase" as used herein, refer to at least about 10%, at least about 20%, at least about 30%, at least about 40%, at least about 50%, at least about 60%, at least about 70%, at least about 80%, at least about 90% or at least about 100% higher level of pAkt level or pAkt:tAkt ratio in the subject following treatment as compared to a level of same in a subject prior to treatment or to commonly used control samples taken from sick individual (e.g. an individual with a disease, e.g. ALS, corresponding to the subject being treated).

In another aspect, the present invention includes a method for determining the efficacy of treatment for a neurodegenerative disease in a subject in need thereof, the method comprises determining in a sample from the subject whether a composition comprising a therapeutically effective amount of a peptide comprising an amino acid sequence selected from the group consisting of SEQ ID NO: 1, SEQ ID NO: 2 and an analog or a derivative thereof induces an increase in the level of pAkt and pAkt:tAkt ratio. According to the principles of the present invention, an increase in the level of pAkt and pAkt:tAkt ratio indicates that the subject will show responsiveness to treatment with said peptide.

In some embodiments, the level of pAkt:tAkt ratio (also denoted "pAkt/tAkt" standing for phosphorylated Akt divided by total Akt) in said bodily sample is evaluated, wherein responsiveness to treatment is determined for a subject having a pAkt/tAkt ratio which is significantly lower than a corresponding control value.

As used herein, the terms "below" or "lower" as used herein, refer to at least about 10%, at least about 20%, at least about 30%, at least about 40%, at least about 50%, at least about 60%, at least about 70%, at least about 80%, at least about 90% or at least about 100% lower level of pAkt level or pAkt:tAkt ratio in the subject following treatment as compared to a level of same in a control sample (e.g. a sample taken from healthy individual).

Preferably, the control value corresponds to pAkt level or pAkt/Akt ratio in a sample derived from a healthy individual, or from a panel of control samples obtained from a set of healthy individuals, or from a stored set of data corresponding to control individuals (e.g. healthy individuals or individuals that are not afflicted with neurodegenerative disease, particularly ALS).

According to yet another embodiment, the control value corresponds to pAkt level in a sample derived from a bodily sample of an individual afflicted with a neurodegenerative disease, e.g. ALS, but manifesting a milder version of the disease according to measureable criteria (e.g. slowly progressing disease).

In the methods of the invention, the terminology of "significant reduction", "significant decline", "significantly below" and the like, in the level or amount of pAkt of an individual, is interchangeable and refers to a statistically significant reduction recognized by a skilled artisan, as compared to control. Statistical significance may be evaluated by any method known in the art, such as, Student's T-test, Analysis of variance (ANOVA) and Chi-square test, among others.

The present invention also highlights the use of Akt phosphorylation as a biomarker. Specifically, the present invention provides a method for assessing whether the progression of ALS is slow or rapid.

By "rapid progression" or "rapid disease" it is meant that the symptoms of ALS progress continuously and significant degradation of motor neurons can be observed within less than a year. Rapid disease in human patients corresponds to survival of up to 4 years from diagnosis. In contrast, "slow progression" or "slow disease" refers to a condition where the ALS symptoms appear slowly with long periods, i.e. many months or years. Slow disease in human patients also typically corresponds to survival of more than 4 years from diagnosis.

According to one embodiment, there is provided a method for prognosticating the progression of amyotrophic lateral sclerosis (ALS) in an ALS patient, comprising (a) assessing the value of at least one marker selected from: pAkt and pAkt:tAkt ratio, in a bodily sample derived from the ALS patient; and (b) obtaining the ratio between the value of said marker and the value of the marker in a control sample, wherein a level of pAkt or pAkt:tAkt ratio significantly below a control value indicates a rapid disease.

The present invention further provides kits suitable for use in methods of the invention. Specifically, the present invention provides kits for diagnosing neurodegenerative diseases and kits for diagnosing ALS. In addition, the present invention provides kits for prognosticating the progression of neurodegenerative diseases and kits for prognosticating the progression of ALS in an ALS patient.

A kit according to the present invention preferably comprises i) means for collecting a bodily sample from a subject ii) means for determining the level of the markers pAkt and tAkt (total Akt) in the sample and iii) a standard sample for comparison of the tested sample.

In certain embodiments, the means for determining the levels of said markers comprise at least one antibody directed to pAkt and at least one antibody directed to total Akt. In some embodiments, the level of pAkt and tAkt are determined by Western blot analysis, or applying Akt phosphorylation assays as been demonstrated by Armentero et al. (Neurobiol Aging, Jan. 25, 2010). In other embodiments, the level of pAkt and tAkt are determined by FACS (fluorescence-activated cell sorting) assays.

According to one embodiment, the kits further comprise a standard, a calibration curve or an index indicating a control value of the pAkt and the tAkt.

Typically a control value corresponds to pAkt level or pAkt:tAkt ratio in a sample comprising a bodily sample of a healthy individual, a bodily sample of an individual not afflicted with any neurodegenerative disease, such as ALS, a bodily sample of an individual afflicted with a slowly progressing neurodegenerative disease, such as ALS.

The kits for prognosticating the progression of ALS, may preferably comprise (a) means for determining pAkt levels and tAkt level in a bodily sample, such as, a bodily sample derived from the peripheral or lymphatic systems, (b) means for determining pAkt levels in and tAkt level in a bodily sample derived from the muscles of a subject and iii) a standard sample for comparison of the tested sample.

In certain embodiments, the detection of pAkt and tAkt may be performed using an immunoassay such as an enzyme-linked immunosorbent assay (ELISA) testing kit. In such assays samples are typically incubated in the presence of an immobilized first specific binding agent (e.g. an antibody) capable of specifically binding pAkt or an immobilized first specific binding agent capable of binding tAkt. Binding of pAkt or tAkt to said first specific binding agent may be measured using any one of a variety of known methods, such as using a labeled second specific binding agent capable of specifically binding pAkt or tAkt, respectively, (at a different epitope) or capable of specifically binding the first specific binding agent.

Exemplary specific binding agents include e.g. monoclonal antibodies, polyclonal antibodies, and antibody fragments such as recombinant antibody fragments, single-chain antibodies (scFv) and the like.

Exemplary anti-pAkt antibodies which may be used in accordance with the present teachings may be commercially purchased from e.g. Cell Signaling Technology (e.g. #9275), Millipore (e.g. STAR phospho-Akt1 (Thr308) ELISA kit), BioLegend and Epitomics Inc.

Exemplary anti-tAkt antibodies (i.e. anti-Akt antibodies) which may be used in accordance with the present teachings may be commercially purchased from e.g. Cell Signaling Technology (e.g. #9272), Millipore (e.g. STAR Akt ELISA kit), Enzo Life Sciences Inc., BioLegend and Proteintech Group Inc.

In some embodiments, various conventional tags or labels may be used, such as a radioisotope, an enzyme, a chromophore or a fluorophore. A typical radioisotope is iodine-125 or sulfur-35. Typical enzymes for this purpose include horseradish peroxidase, horseradish galactosidase and alkaline phosphatase.

Alternately, other immunoassays may be used; such techniques are well known to the ordinarily skilled artisan and have been described in many standard immunology manuals and texts.

In some embodiments, the methods of the invention are suitable for automated or semi-automated analysis, and may enable clinical, medium or high-throughput screening of multiple samples. For example, automated ELISA systems such as Biotest's Quickstep® ELISA Processor, Maxmat Automated microwell ELISA analyzer (Maxmat S.A., France), or DSX™ Four-Plate System (Dynex Technologies) may conveniently be used.

Other suitable assays include for example flow cytometry assays (such as singleplex and multiplex bead-based Luminex® assays (Invitrogen).

Alternately, pAkt or tAkt may be captured on an antibody microarray. The antibody microarray comprises an anti-pAkt antibody or an anti-tAkt antibody, or, for example, a combination of anti-pAkt antibodies and anti-tAkt antibodies. In general, the sample (e.g., peripheral blood) obtained from the subject is placed on the active surface of a chip for a sufficient time to allow binding. Then, unbound molecules are washed from the surface using a suitable eluant, such as phosphate buffered saline. In general, the more stringent the eluant, the more tightly pAkt or tAkt must be bound to be retained after the wash. As a result, the retained pAkt or tAkt can be detected by appropriate means.

Additional exemplary assays may be based on dipstick technology, as demonstrated, for example, in U.S. Pat. Nos. 4,632,901; 4,313,734; 4,786,589 5,656,448 and EP 0125118. For example, U.S. Pat. No. 4,632,901, discloses a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample. EP 0125118 discloses a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

For example, the method may be performed by the steps comprising:
a) collecting a bodily sample from the subject;
b) contacting the sample, under conditions such that a specific antigen-antibody complex may be formed, with at least one antibody, said antibody being directed to either pAkt or tAkt;
c) quantifying the amount of antigen-antibody complex formed, wherein said amount is indicative of the amount of pAkt or tAkt in said sample.

An antibody "directed to" an antigen, as used herein is an antibody which is capable of specifically binding the antigen. The term "specifically bind" as used herein means that the binding of an antibody to an antigen is not competitively inhibited by the presence of non-related molecules. Antibodies directed to pAkt and antibodies directed to tAkt may be prepared using well known methods, for example as detailed hereinabove. Alternatively, antibodies, or ELISA kits for determining the presence of these antigens, may be purchased from a variety of sources.

The following examples are to be considered merely as illustrative and non-limiting in nature. It will be apparent to one skilled in the art to which the present invention pertains that many modifications, permutations, and variations may be made without departing from the scope of the invention.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

The Effect of the Peptide of SEQ ID NO: 1 on the Akt Pathway in Cells

Raw264.7 macrophages were treated with 50 mM of the peptide having the amino acid sequence of SEQ ID NO: 1 ($10x^5$ per well) in quadruplicates. Akt phosphorylation was found to be induced shortly after introduction of the peptide (FIG. 1A). Akt and pAkt were detected using western blot analysis with Cell Signaling Technology #9272 and #9275 antibodies. This observation demonstrates that the peptide triggers activation of the Akt pathway in a specific manner.

Next, mice were injected with the peptide of SEQ ID NO: 1 (400 μl) and after 30 minutes lymph nodes were assessed for pAkt, compared to lymph samples obtained from non-treated mice. Akt phosphorylation was measured using ELISA compared to a standard, using Millipore's STAR Akt and STAR phospho-Akt1 (Thr308) ELISA kits.

Figure 1B:
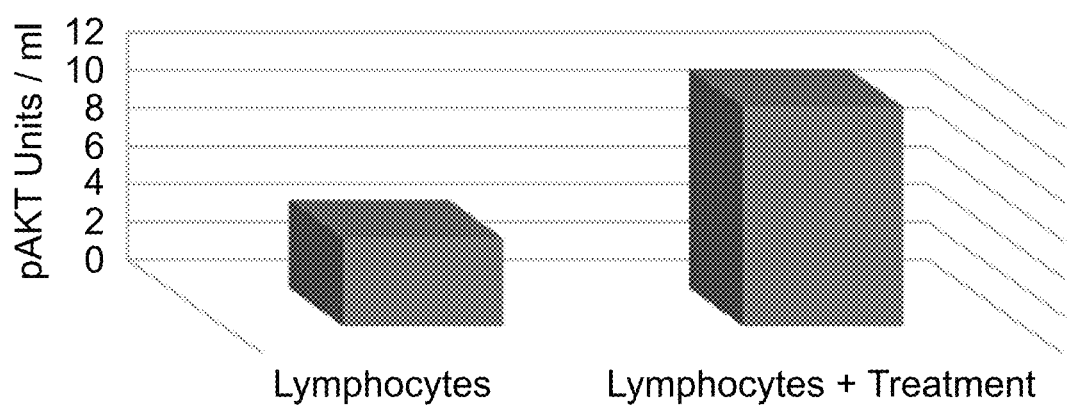
FIG. 1B shows Akt phosphorylation in mice treated with the peptide of SEQ ID NO: 1 as compared to non-treated mice.

As shown in FIG. 1B, Akt phosphorylation was higher in treated mice compared to non-treated mice.

Example 2

The Effect of the Peptide of SEQ ID NO: 1 on Survival of a Mice Model for ALS

ALS is characterized by apoptosis of motor neurons. The SOD1G93A mouse model of familial ALS was used in the following examples. Initially, doses less than optimal were applied, and model irregularities due to gene counts were detected. These deficiencies were repaired in later studies.

Mice were purchased from Jackson and were administered with a dose of at least 200 microgram a day of the peptide of SEQ ID NO: 1. Overall, the studies included 142 mice. Eventually all mice died of neurologic disease. Mice (a few) that died before the detection of a symptomatic disease were not included, as recommended by Scott et al. (Amyotroph Lateral Scler. 2008; 9(1):4-15). Of the 142 mice, 99 mice were treated intraperitoneally (IP), intranasally (IN), intravenously (IV) or with a combined delivery, and 43 mice were used as control (untreated or treated with PBS).

Allocation of the mice to the experimental groups was done by matching weight and, when applicable (particularly in study III) also by gender match. In studies II and III, where treatment started after disease onset, the primary grouping criteria was date of onset. In fact, age at onset and weight at onset reflect to a certain degree the disease severity, thereby allowing to perform an even distribution of animals according to the phenotypic manifestation of the disease. Although genotypic distribution and separation of siblings is recommended, siblings in the same groups were used, preferring the phenotypic criteria as an indicator of the severity of the disease itself, and as in many cases too many of the mice were from the same pedigree.

Exclusion (censoring) criteria were employed to exclude data that do not include any measurements taken from animals that died before detection of the neurological damage or animals that died due to non-disease associated reasons (such as physical wounds).

In this example, 40 female mice (purchased from Jackson) were included. 30 mice were treated (IN or IV; peptide of SEQ ID NO: 1) and 10 mice were controls. Disease onset was measured by Rotarod exertion value (measuring mobility on a Rotarod vs. time), defined as Rotarod values below 180 (i.e. 3 min.). The animals were divided into groups according to weight match.

TABLE 1

Study design

| Group | Treatment | Route | Schedule | Age at treatment initiation | n |
|---|---|---|---|---|---|
| 1 | PBS (control) | IV | Daily | 75 days | 10 |
| 2 | 200 µg peptide | IV | Daily | 75 days | 10 |
| 3 | 400 µg peptide | IV | Daily | 75 days | 10 |
| 4 | 400 µg peptide | IN | Daily | 75 days | 10 |

TABLE 2

Total survival of mice treated with the peptide

| Group | Survival of 50% (days) | Survival Mean (days) | P (Logrank) | Added survival compared to control (days) |
|---|---|---|---|---|
| Control | 125 | 128.1 | | — |
| 400 IN | 139 | 132.4 | | 4-14 |
| 200 IV | 145 | 144.3 | 0.02 | 16-20 |
| 400 IV | 139 | 136.2 | | 8-14 |
| All treatment groups | 139 | 139.2 | 0.017* | 11-14 |

*Significance equivalent to p = 0.05 for 3 combined groups

Figure 2:
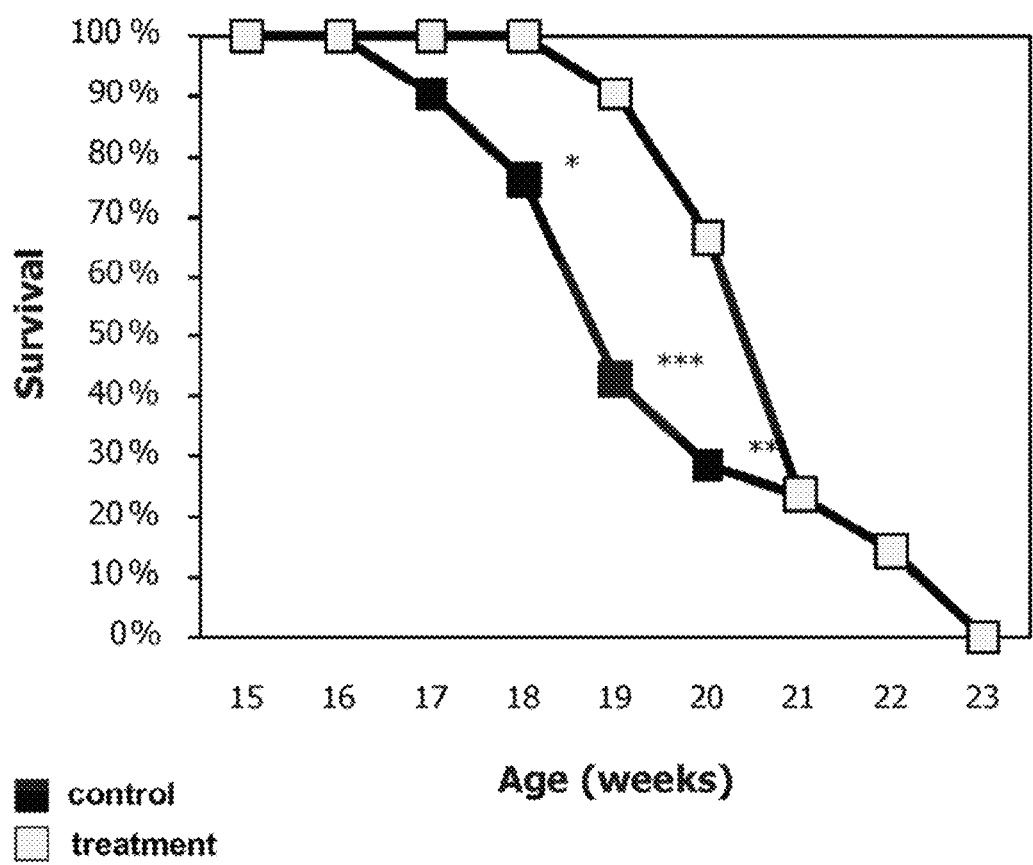
FIG. 2 shows survival curve after disease onset (week 15 onwards) of treated (light squares) and untreated (control; dark squares) SOD1 mice together with the extent of significance, as evaluated by Chi test (* for $P=<0.05$;  for $P=<0.01$ and * for $P=<0.001$). Mice were treated with the peptide of the invention starting at disease onset as indicated by weigh loss (average—90 days, 400 µg 200 IP+200 IV) and were compared to control (n=21+21) mice (untreated or treated with PBS).

The results summarized in Table 2 above clearly indicate that the peptide of the invention induces a significant (p=0.05) increase in survival, additional 11 to 14 days as compared to control, irrespective of the disease stage. The significantly prolonged survival induced by the peptide of the invention is also shown in FIG. 2.

Similar results are shown in the 'all stages' columns of Table 3, below. As detailed in Table 3, the most pronounced effect of the protein of the invention is exerted during late stages of the disease, which is characterized by low Rotarod index (less than 120).

TABLE 3

Disease duration at different stages of the disease (late and early) upon treatment with the peptide of the invention at 200 µg or 400 µg for 7 successive days$^a$

| Group | Late disease (Y < 120)$^a$ Duration (days) | Early disease (180 > Y > 120)$^b$ Duration (days) | All stages of the disease Duration (days) |
|---|---|---|---|
| 400 µg IN (n = 10) | 26.9 | 17.7 | 44.6 |
| 200 µg IV (n = 10) | 34.8 | 16.2 | 51.0 |
| 400 µg IV (n = 10) | 25.7 | 15.8 | 41.5 |
| All treatments (n = 30) | 29.2 | 16.6 | 45.7 |
| Control (10) | 15.5 | 15.7 | 31.2 |

$^a$Mice stayed on the Rotarod for less than 120 seconds, i.e. Rotarod index (Y) < 120.

$^b$Mice that stayed on the Rotarod for more than 120 seconds but less than 180 seconds.

The results indicate that daily treatments with the peptide of the invention via any way of administration (IN or IV) leads to increased survival at advanced (late) stages of the disease (measured by Rotarod exertion values below 120 seconds). Treatment with the peptide of the invention prolonged the duration at the late stage by 88% while not affecting disease onset or disease progression at the earlier stages. In this study, onset in all groups was at an average age of 93-97 days, and there were no differences between the groups. Late-stage disease started at age of about 110 days.

In another study (FIG. 2) the differences between 21 mice treated with 400 microgram (200 IP+200 IV) of the SEQ ID NO: 1 peptide and 21 non-treated mice are observed in weeks 18-20. At week 18, 21/21 treated vs. 16/21 non-treated manifested at 20% difference in survival (*, P=0.02); at week 19, 19/21 treated vs. 9/21 non-treated manifested 50% difference in survival (*, P=0.001); and at week 20, 14/21 treated vs. 6/21 non-treated manifested a 40% difference in survival (, P=0.005).

The following analysis (Table 4, below) shows the effect of the peptide of the invention on all treatments, irrespective of the stage of disease, but subject to the method of administration.

TABLE 4

Summary of 50% survival in all groups (treatments and control)

| Study | Treatment | Age at treatment initiation (days) | No. of Treatment animals (number of groups) | No. of Control animals (number of groups) | Average ± SD of added survival (days) | Significance (Logrank) | Average added 50% survival |
|---|---|---|---|---|---|---|---|
| Total | 200-600 μg IP/IV/IN | 89.75 | 99 (9) | 43 (3) | *7.2 ± 12.6 | 0.008 | 10 |

§Disease onset was observed
*Adjusted according to control values

The data shows that the 50% survival of the 99 mice treated with the peptide of SEQ ID NO: 1 was about 10 days longer, significantly (P=0.008) as compared to control. The most effective route of administration seems to be a combined IV/IP administration.

Example 3

The Effect of the Peptide of the Invention on Disease Progression

The protective effect of the peptide of the invention is not only limited to prolonged survival, but also involves significant delay in the progression of disease symptoms, as monitored by the neurologic disability score, thereby postponing development of end-stage disease.

Figure 3:
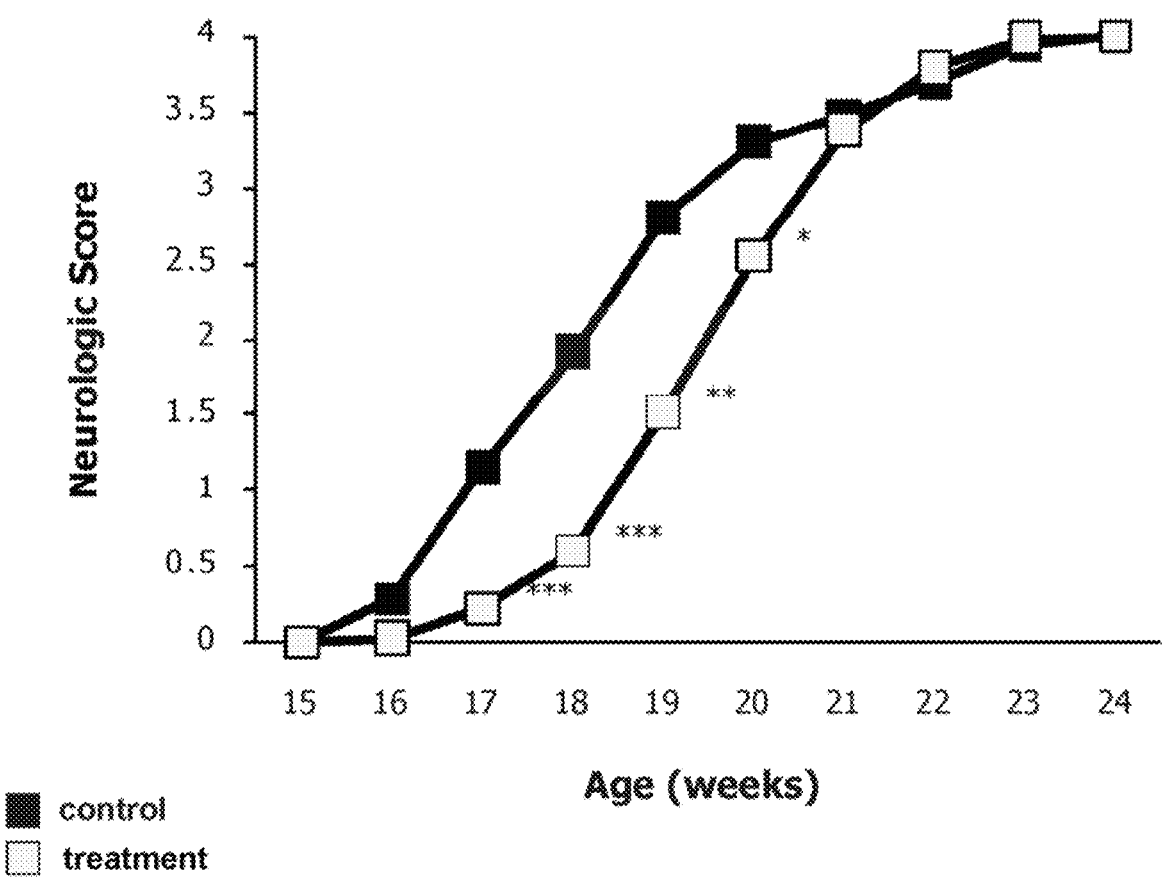
FIG. 3 exhibits the average neurologic disability score in treated (light squares) and untreated (control; dark squares) SOD1 mice together with the extent of significance, as evaluated by Student's T test (* for $P=<0.05$;  for $P=<0.01$ and * for $P=<0.001$). Mice were treated with the peptide of the invention starting at disease onset (average 90 days, 400 µg 200 IP+200 IV) and were compared to control (n=21+21) mice (untreated or treated with PBS).

Mice were administered with the peptide of SEQ ID NO: 1 or placebo (PBS) starting at disease onset as measured by weight loss. It was at average age of about 90 days. The mice were treated daily. During the period of weeks 16-19, the neurologic score was assessed, and was found lower by a factor of about 2 in treated mice compared to controls (FIG. 3).

Example 4

The Effect of the Peptide of SEQ ID NO: 1 on the Akt Pathway In Vivo

Twenty SOD1 mice at the age of 75 days (i.e. prior to disease onset) were treated daily with 200 μg IV+200 μg IP of the peptide of SEQ ID NO: 1 or with PBS, and monitored for body weight and neurological score. At the age of 120 days, the mice were sacrificed, and phosphorylated Akt (pAkt) and total Akt (tAkt) in lymphocytes (lymph node) and muscle cells (hind legs) were measured (see Tables 5-6, below). Two treated mice died prior to age 120 days without any preceding signs of neurologic damage. Two non-treated mice died prior to age 120 days after detection of severe signs of neurologic disease.

TABLE 5

The effect of the peptide of SEQ ID NO: 1 on Akt phosphorylation

| | Muscles | | Lymph node | |
|---|---|---|---|---|
| | pAkt | pAkt/tAkt | pAkt | pAkt/tAkt |
| Control (n = 8) | 150 | 1.61 | 95 | 0.96 |
| SEQ ID NO: 1 (n = 8) | 149 | 1.83 | 129 | 1.35 |
| Difference | −1% | +14% | +36% | +42% |

TABLE 6

Treatment with the peptide of SEQ ID NO: 1 significantly increases the combined pAkt/Akt ratio of lymph nodes and muscles

| Treatment | Lymph node pAKT ratio | Muscle pAKT ratio | Average pAKT | Average pAKT ratio | Percentage of mice with high pAkt content |
|---|---|---|---|---|---|
| PBS | 0.96 | 1.61 | 121 | 1.27 | 12.5% |
| SEQ ID NO: 1 | 1.35 | 1.83 | 140 | 1.61 | 62.5% |
| Percent change | 42% | 14% | 16% | 26% | |
| P value | 0.11 | 0.45 | 0.037 | 0.07 | 0.04 chi square |

The peptide of SEQ ID NO: 1 increased the phosphorylation level of lymphocytes by 36%, and even more in terms of the pAkt/tAkt ratio (42%). There was a minimal effect on muscle cells, which were predominantly highly phosphorylated (70% higher pAkt/tAkt ratio in muscles compared to lymphocytes, before treatment with the peptide of the invention). The average increase of pAkt in both muscles and lymphocytes was statistically significant −P=0.04.

Preliminary measurements of weight loss and neurologic score among non-treated mice with naturally elevated peripheral (muscle and lymph) pAkt showed differences in clinical parameters, as detailed in Table 7, below. This table demonstrates that low lymphocyte and muscle pAkt corresponds to rapid disease (characterized by high neurologic score and weight loss at 120 days) wherein relatively high lymphocyte pAkt and muscle pAkt corresponds to slow disease (i.e. a disease characterized by low neurologic score and weight loss at 120 days).

It is to be understood that a combination of weight loss and neurological score is considered one of the most reliable and gentle (i.e. not introducing additional stressors) ways to assess the presence, progression and staging of ALS.

TABLE 7

The effect of Akt phosphorylation on disease parameters in non-treated SOD1 mice aged 120 days.

| | Muscle pAkt | Lymphocyte pAkt | Muscle-lymph pAkt | Neurologic score | Previous week weight loss |
|---|---|---|---|---|---|
| Lower peripheral pAkt (3) | 138 | 94 | 116 | 0.67 | 4.7% |
| Higher peripheral pAkt (3) | 151 | 111 | 131 | 0.33 | 1.4% |
| Change | +9% | +18% | +13% | −50% | −71% |

The correlation of Akt phosphorylation with disease progression is even more striking when peripheral (muscle and lymph) pAkt of mice with rapid disease, both treated and non-treated, is compared to peripheral pAkt of mice with slow disease, in both treated and non-treated SOD1 mice, as described in Table 8 below.

TABLE 8

The effect of Akt phosphorylation on rapid and slow disease

|  | Neurologic score | Muscle + lymph pAkt |
|---|---|---|
| Score 0.5-1.25 (n = 7, SOD1 mice with Rapid Disease) | 0.8 | 120 |
| Score 0-0.25 (n = 9, SOD1 mice with Slow Disease) | 0.05 | 139 |
| Significance |  | P = 0.01 |

In this study, animals at day 120 were divided into groups by the disease state. The results of this analysis indicate that the pAKT correlates with the state of the disease.

Specifically, in mice where the disease progressed rapidly (neurological score of 0.8 at 120 days), the ratio of muscle: lymph pAkt is significantly (P=0.01) lower than this ratio in mice where the disease progressed slowly (neurological score of 0.05 at 120 days). Thus, the results indicate that pAkt phosphorylation is a reliable indication for distinguishing the stage of the ALS disease (slow/fast).

When these mice were divided according to pAkt ratio of lymph node and muscle, 10 mice with low pAkt had a significantly (P=0.005) 10 times higher clinical score (0.6) as compared to 6 mice with high pAkt (0.06).

Thus, the peptide of the invention might employ increased pAkt in both muscles and lymphocytes for reduction of ALS progression rate in SOD1 mice, and might contribute to the treatment of sporadic ALS.

Example 5

Responsiveness to Treatment

The following analysis reflects the significant therapeutic effect of the peptide of the invention on ALS and emphasizes the importance in assessing responsiveness to treatment in terms of increased biomarker during the treatment.

Mice, age 75 days, were treated for 45 days with 400 μg of the peptide of SEQ ID NO: 1, administered as follows: 200 μg IV and 200 μg IP. At age of 120 days, 6 of the peptide treated mice responded to treatment, having a slow disease e.g. low weight loss (only 3.3%) and low neurological score (0.08) compared to placebo (PBS) treated mice which kept losing weight, reaching a weight loss of 5.4% and neurological score of 0.8. The six responding mice had 49% higher pAkt (P=0.01) compared to the placebo treated mice.

Two other mice treated with the peptide of the invention did not respond to treatment, having a significantly higher neurological score of 1.1 (93%; P=0.05) and higher weight loss (6.3%). Those mice resulted with a significantly lower pAkt phosphorylation (−37%; P=0.004 in comparison with the responding group).

The data is summarized in Table 9, below.

TABLE 9 pAkt in responding and non-responding SOD1 mice at 120 days

|  | Lymphocyte pAkt | Effect on pAkt* | Average score (age 110-120 days) | Effect on score** | Weight loss§ |
|---|---|---|---|---|---|
| Placebo (PBS; n = 10) | 95 (8 survivors, 2 died earlier) | 100% | 0.8 | 100% | 5.4% |
| Responding (SEQ ID NO: 1; n = 6) | 142 | +49% pAkt* P = 0.01 | 0.08 | −90% score* P = 0.02 | 3.3% |
| Non responding (SEQ ID NO: 1; n = 2) | 90 | −37% pAkt** P = 0.004 | 1.1 | +1400%** score P = 0.05 | 6.3% |

*The effect of treatment on pAkt and neurologic score relative to placebo (100%).
**The effect of treatment on pAkt and neurologic score in non-responders relative to responders
§Average weight loss (compared to the weight on the week prior to treatment)

Example 6

Measuring the Effect of the Peptide of SEQ ID NO: 1 on Slow and Rapid Disease

SOD1 mice were treated IP and IV using the peptide of SEQ ID NO: 1 starting at disease onset, detected by weight loss, at an average age of 90 days.

In order to check if mice with rapid disease respond to treatment differently from mice with slow disease, a comparison was made separately of the 50% control and treated mice that survived less than or equal to the median survival and 50% control and treated mice that survived longer than the median survival.

According to this comparison, demonstrated in Table 10 below, SD values were 40% lower for treated mice, demonstrating that treatment reduced the diversity and range between rapid and slow disease, making the rapid disease look more like slow disease, and the extension of survival was much larger (11 days comparing to 3 days), and much more significant (P=0.0001 compared to P=0.8), for mice with fast disease.

TABLE 10

Systemic treatment with the peptide of SEQ ID NO: 1 starting at the onset of weight loss (age 90 days)

|  | N control/ treatment | SD control/ treatment | 50% fast control/ treatment | 50% slow control/ treatment |
|---|---|---|---|---|
| PBS | 21 | 13.8 | 125.2 | 146.7 |
| SEQ ID NO: 1 | 21 | 8.7 | 136.0 | 149.7 |
| Significance |  |  | P = 0.0001 | P = 0.8 |

The absence of an effect on long-term survivors was also reflected by the survival and disease progression curves: they showed the convergence of control and treatment curves for long-term surviving mice and at late study stages, which demonstrate the lack of effect on the fraction of 25% of mice with the longest survival (FIGS. 2 and 3).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating a subject suffering from amyotrophic lateral sclerosis (ALS), the method comprising:
   (a) assessing the level of phosphorylated Akt (pAkt) or pAkt:total Akt (tAkt) ratio in a bodily sample derived from a candidate subject suffering from ALS so as to obtain a control value of a pAkt level or a control value of a pAkt:tAkt ratio;
   (b) administering a peptide comprising an amino acid sequence as set forth in SEQ ID NO: 1 or SEQ ID NO: 2 to the candidate subject;
   (c) reassessing the level of phosphorylated Akt (pAkt) or pAkt:total Akt (tAkt) ratio in a bodily sample derived from the subject following said administering, wherein responsiveness to treatment by said peptide is indicated by a pAkt level or pAkt:tAkt ratio significantly above said control value of a pAkt level or said control value of pAkt:tAkt ratio, wherein said assessing is carried out using an antibody which specifically binds pAkt and not non-phosphorylated Akt and an antibody which specifically binds tAkt; and
   (d) administering the peptide to a responsive subject, assessed according to (c).

2. The method according to claim 1, wherein the bodily sample is derived from the peripheral blood, the lymph system or a muscle of said subject.

3. The method according to claim 2, wherein said peripheral blood or said lymph system comprises lymphocytes.

* * * * *